(12) United States Patent
Lu et al.

(10) Patent No.: US 7,902,353 B2
(45) Date of Patent: *Mar. 8, 2011

(54) NUCLEIC ACID ENZYME BIOSENSORS FOR IONS

(75) Inventors: Yi Lu, Champaign, IL (US); Jing Li, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 746 days.

This patent is subject to a terminal disclaimer.

(21) Appl. No.: 11/674,042

(22) Filed: Feb. 12, 2007

(65) Prior Publication Data

US 2008/0176228 A1    Jul. 24, 2008

Related U.S. Application Data

(60) Continuation of application No. 10/702,676, filed on Nov. 6, 2003, now Pat. No. 7,192,708, which is a division of application No. 09/605,558, filed on Jun. 27, 2000, now Pat. No. 6,706,474.

(51) Int. Cl.
*C12Q 1/68* (2006.01)
*C07H 21/04* (2006.01)

(52) U.S. Cl. ............ 536/24.5; 435/325; 435/375; 435/91.31; 435/6; 536/23.1

(58) Field of Classification Search ............ None
See application file for complete search history.

(56) References Cited

U.S. PATENT DOCUMENTS

| | | | |
|---|---|---|---|
| 4,362,603 A | 12/1982 | Presson et al. | |
| 4,703,017 A | 10/1987 | Campbell et al. | |
| 4,746,631 A | 5/1988 | Clagett | |
| 4,855,240 A | 8/1989 | Rosenstein et al. | |
| 4,857,319 A | 8/1989 | Crowe et al. | |
| 5,008,109 A | 4/1991 | Tin | |
| 5,459,040 A | 10/1995 | Hammock et al. | |
| 5,472,881 A | 12/1995 | Beebe et al. | |
| 5,580,967 A | 12/1996 | Joyce | |
| 5,593,835 A | 1/1997 | Rando et al. | |
| 5,631,148 A | 5/1997 | Urdea | |
| 5,663,064 A | 9/1997 | Burke et al. | |
| 5,807,718 A | 9/1998 | Joyce et al. | |
| 5,807,967 A | 9/1998 | Snow et al. | |
| 5,910,408 A | 6/1999 | Szostak et al. | |
| 5,989,813 A | 11/1999 | Gerdes | |
| 6,040,138 A | 3/2000 | Lockhart et al. | |
| 6,110,462 A | 8/2000 | Barbas et al. | |
| 6,159,347 A | 12/2000 | Sumner, Jr. et al. | |
| 6,287,765 B1 | 9/2001 | Cubicciotti | |
| 6,316,194 B1 | 11/2001 | Karn et al. | |
| 6,326,508 B1 | 12/2001 | Godbole et al. | |
| 6,361,944 B1 | 3/2002 | Mirkin et al. | |
| 6,387,617 B1 * | 5/2002 | Asher et al. ............ 435/6 |
| 6,426,335 B1 | 7/2002 | Janjic et al. | |
| 6,451,535 B1 | 9/2002 | Jenne et al. | |
| 6,485,982 B1 | 11/2002 | Charlton | |
| 6,541,617 B1 | 4/2003 | Bamdad et al. | |
| 6,630,306 B1 | 10/2003 | Breaker | |
| 6,706,474 B1 | 3/2004 | Lu et al. | |
| 6,818,455 B2 | 11/2004 | May et al. | |
| 6,843,890 B1 | 1/2005 | Godbole | |
| 6,849,414 B2 | 2/2005 | Guan et al. | |
| 6,890,719 B2 | 5/2005 | Lu et al. | |
| 7,109,165 B2 | 9/2006 | Matulic-Adamic et al. | |
| 7,192,708 B2 | 3/2007 | Lu et al. | |
| 7,332,283 B2 | 2/2008 | Lu et al. | |
| 7,612,185 B2 | 11/2009 | Lu et al. | |
| 7,799,554 B2 | 9/2010 | Mazumdar et al. | |
| 2003/0215810 A1 | 11/2003 | Lu et al. | |
| 2003/0235611 A1 | 12/2003 | Ehringer et al. | |
| 2004/0018515 A1 | 1/2004 | Diener et al. | |
| 2004/0110167 A1 | 6/2004 | Gerdes et al. | |
| 2004/0126882 A1 | 7/2004 | Ellington et al. | |
| 2004/0175693 A1 | 9/2004 | Lu et al. | |
| 2005/0037075 A1 | 2/2005 | Farokhzad et al. | |
| 2005/0136500 A1 | 6/2005 | Yang et al. | |
| 2005/0282186 A1 | 12/2005 | Lu et al. | |
| 2006/0019406 A1 | 1/2006 | Wei et al. | |
| 2006/0045910 A1 | 3/2006 | Ehringer | |
| 2006/0094026 A1 | 5/2006 | Lu et al. | |

(Continued)

FOREIGN PATENT DOCUMENTS

EP    121970    10/1984

(Continued)

OTHER PUBLICATIONS

Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).

Andreola, M-L., et al., "DNA aptamers selected against the HIV-1 RNase H display in vitro antiviral activity"., Biochemistry, vol. 40, No. 34, pp. 10087-10094, (2001).

Bain, C. D., et al., "Modeling organic surfaces with self-assembled monolayers"., Angew. Chem. Int. Ed. Engl., vol. 28, No. 4, pp. 506-512, (1989).

Been, M.D., et al., "Self-cleaving ribozymes of hepatitis delta virus RNA"., Eur. J. Biochem., vol. 247, pp. 741-753, (1997).

Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

(Continued)

*Primary Examiner* — James (Doug) Schultz
(74) *Attorney, Agent, or Firm* — Evan Law Group LLC

(57) ABSTRACT

Disclosed are compositions and methods for the sensitive and selective detection of ions using nucleic acid enzymes.

14 Claims, 11 Drawing Sheets

U.S. PATENT DOCUMENTS

| | | |
|---|---|---|
| 2006/0166222 A1 | 7/2006 | Lu et al. |
| 2007/0037171 A1 | 2/2007 | Lu et al. |
| 2007/0269821 A1 | 11/2007 | Mazumdar et al. |
| 2008/0176228 A1 | 7/2008 | Lu et al. |
| 2009/0011402 A1 | 1/2009 | Lu et al. |
| 2009/0029874 A1 | 1/2009 | Lu et al. |
| 2009/0197261 A1 | 8/2009 | Lu et al. |
| 2010/0105039 A1 | 4/2010 | Lu et al. |
| 2010/0151579 A1 | 6/2010 | Wang et al. |
| 2010/0166842 A1 | 7/2010 | Lu et al. |

FOREIGN PATENT DOCUMENTS

| | | |
|---|---|---|
| EP | 1219708 | 7/2002 |
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Blake, D.A., et al., "Antibody-based sensors for heavy metal ions"., Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).

Bock, L.C., et al., "Selection of single-stranded DNA molecules that bind and inhibit human thrombin"., Nature, vol. 355, pp. 564-566, (1992).

Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).

Breaker, R.R., "Catalytic DNA: in training and seeking employment"., Nature Biotechnology, vol. 17, pp. 422-423, (1999).

Breaker, R.R., "DNA enzymes"., Nature Biotechnology, vol. 15, pp. 427-431, (1997).

Breaker, R.R., "Molecular Biology: Making Catalytic DNAs"., Science, vol. 290, issue 5499, pp. 2095-2096, (2000).

Breaker, R.R., et al., "A DNA enzyme that cleaves RNA"., Chemistry & Biology, vol. 1, No. 4, pp. 223-229, (1994).

Breaker, R.R., et al., "A DNA enzyme with $Mg^{2+}$-dependent RNA phosphoesterase activity"., Chemistry & Biology, vol. 2, No. 10, pp. 655-660, (1995).

Breaker, R.R., et al., "Engineered allosteric ribozymes as biosensor components"., Current Opinion in Biotechnology, vol. 13, pp. 31-39, (2002).

Brody, E.N., et al., "Aptamers as therapeutic and diagnostic agents"., Reviews in Molecular Biotechnology, vol. 74, pp. 5-13, (2000).

Broude, N. E., "Stem-loop oligonucleotides: a robust tool for molecular biology and biotechnology", Trends in Biotechnology, vol. 20, No. 6, pp. 249-256, (2002).

Brown, A.K., et al., "A lead-dependent DNAzyme with a two-step mechanism"., Biochemistry, vol. 42, No. 23, pp. 7152-7161, (2003).

Bruesehoff, P.J., et al., "Improving metal ion specificity during In Vitro selection of catalytic DNA"., Combinatorial Chemistry & High Throughput Screening, vol. 5, pp. 327-335, (2002).

Bruno, J.G., et al., "In vitro selection of DNA aptamers to anthrax spores with electrochemiluminescence detection"., Biosensors & Bioelectronics, vol. 14, pp. 457-464, (1999).

Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).

Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).

Burgstaller, P., et al., "Isolation of RNA aptamers for biological cofactors by in vitro selection"., Angew. Chem. Int. Ed. Engl, vol. 33, No. 10, pp. 1084-1087, (1994).

Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).

Burke, D.H., et al., "A Novel Acidophilic RNA Motif That Recognizes Coenzyme A"., Biochemistry, vol. 37, No. 13, pp. 4653-4663, (1998).

Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).

Burke, D.H., et al., "RNA aptamers to the peptidyl transferase inhibitor chloramphenicol"., Chemistry & Biology, vol. 4, No. 11, pp. 833-843, (1997).

Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).

Burwell Jr., R.L., "Modified silica gels as adsorbents and catalysts"., Chemical Technology, 4, pp. 370-377, (1974).

Cadwell, R.C., et al., "Mutagenic PCR"., PCR Methods and Applications, vol. 3, pp. S136-S140, (1994).

Cadwell, R.C., et al., "Randomization of genes by PCR mutagenesis"., PCR Methods and Applications, vol. 2, pp, 28-33, (1992).

Cao, Y.W., et al., "DNA-modified core-shell Ag/Au nanoparticles"., J. Am. Chem. Soc., vol. 123, No. 32, pp. 7961-7962, (2001).

Carmi, N., et al., "Cleaving DNA with DNA"., Proc. Natl. Acad. Sci. USA, vol. 95, pp. 2233-2237, (1998).

Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs"., Current Opinion in Structural Biology, vol. 4, pp. 618-622, (1994).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: $d(C_4)$"., Biochemistry, vol. 33, No. 46, pp. 13540-13546, (1994).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc, vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issue 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the word "ion" printed from Merriam-Webster online dictionary (www.m-w.com) on Jun. 30, 2004.

Definition of the word "particle" printed from Merriam-Webster online dictionary (www.m-w.com) on Jun. 29, 2004.

Deo, S., et al., "A Selective, Ratiometric Fluorescent Sensor for $Pb^{2+}$"., J. Am. Chem. Soc., vol. 122, No. 1, pp. 174-175, (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1118, (2001).

Doudna, J.A., et al., "The Chemical Repertoire of Natural Ribozymes"., Nature, vol. 418, pp. 222-228, (2002).

Earnshaw, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).

Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).

Fodor, S.P.A., et al., "Light-directed, spatially addressable parallel chemical synthesis"., Science, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with sub-micromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1".,Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE-The international society for optical engineering, vol. 3858, pp. 135-143, (1999).

International Search Report dated Jan. 15, 2003 for corresponding PCT application No. PCT/US01/20557.

International Search Report dated Aug. 1, 2003 for corresponding PCT application No. PCT/US03/08483.

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology, vol. 4, pp. 331-336, (1994).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $ZN^{2+}$"., Journal of Inorganic Biochemistry, vol. 82, pp. 197-206, (2000).

Kiga, D., et al., "An RNA aptamer to the xanthine/guanine base with a distinctive mode of purine recognition"., Nucleic Acids Research, vol. 26, No. 7, pp. 1755-1760, (1998).

Klußmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lee, M., et al., "A fiber-optic microarray biosensor using aptamers as receptors"., Analytical Biochemistry, vol. 282, pp. 142-146, (2000).

Lehman, N., et al., "Evolution in vitro of an RNA enzyme with altered metal dependence"., Nature, vol. 361, pp. 182-185, (1993).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, X., et al., "A fiber-optic evanescent wave DNA biosensor based on novel molecular beacons"., Analytical Chemistry, vol. 71, No. 22, pp. 5054-5059, (1999).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pavlov, V., et al., "Aptamer-functionalized au nanoparticles for the amplified optical detection of thrombin"., J. Am. Chem. Soc., vol. 126, no. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N. A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W. et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionality"., J. Am. Chem. Soc., vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54, No. 1, pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes"., New Journal of Chemistry, vol. 17, pp. 739-755, (1993).

Seetharaman, S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Allosteric nucleic acid catalysts"., Current Opinion in Structural Biology, vol. 10, pp. 318-325, (2000).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Sun, L.Q., et al., "Catalytic nucleic acids: From lab to applications"., Pharmacological Reviews, vol. 52, pp. 325-347, (2000).

Tang, J., et al., "Rational design of allosteric ribozymes"., Chemistry & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N. K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection".,Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Uphoff, K.W., et al., "In vitro selection of aptamers: the dearth of pure reason"., Current Opinion in Structural Biology, vol. 6, pp. 281-288, (1996).

Vaish, N.K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition"., Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis"., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1988).

Werstuck, G., et al., "Controlling gene expression in living cells through small molecule-RNA interactions"., Science, vol. 282, pp. 296-298, (1998).

Whitesides, G.M., et al., "Self-assembled mohnolayers and lithography"., Proceedings of the Robert A. Welch Foundation 39th Conference on Chemical Research on Nanophase Chemistry, pp. 109-121, Houston, TX, Oct. 23-24, 1995.

Wiegand, T.W., et al., "Selection of RNA amide synthases"., Chemistry & Biology, vol. 4, No. 9, pp. 675-683, (1997).

Williams, K.P., et al., "Bioactive and nuclease-resistant L-DNA ligand of vasopressin"., Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot"., Biochemistry, vol. 37, No. 41, pp. 14410-14419, (1998).

Wilson, C., et al., "In vitro evolution of a self-alkylating ribozyme"., Nature, vol. 374, pp. 777-782, (1995).

Wilson, C., et al., "Isolation of a fluorophore-specific DNA aptamer with weak redox activity"., Chemistry & Biology, vol. 5, No. 11, pp. 609-617, (1998).

Wilson, D.S., et al., "In vitro selection of functional nucleic acids"., Annu. Rev. Biochem. vol. 68, pp. 611-647, (1999).

Winkler, J.D., et al., "Photodynamic Fluorescent Metal Ion Sensors with Parts per Billion Sensitivity"., J. Am. Chem. Soc., vol. 120, No. 13, pp. 3237-3242, (1998).

Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).

Yang, Q., et al., "DNA ligands that bind tightly and selectively to cellobiose"., Proc. Natl. Acad. Sci. USA, vol. 95, pp. 5462-5467, (1998).

Yurke, B., et al., "A DNA-fuelled molecular machine made of DNA"., Nature, vol. 406, pp. 605-608, (2000).

Zhang, B., et al., "Peptide bond formation by in vitro selected ribozymes"., Nature, vol. 390, pp. 96-100, (1997).

Zhang, P., et al., "Design of a molecular beacon DNA probe with two fluorophores"., Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).

Zimmerman, J.M., et al., "In vivo selection of spectinomycin-binding RNAs"., Nucleic Acids Research, vol. 30, No. 24, pp. 5425-5435, (2002).

Zimmermann, G.R., et al., "Molecular interactions and metal binding in the theophylline-binding core of an RNA aptamer"., RNA, vol. 6, pp. 659-667, (2000).

Aggarwal, S.K., et al., "Determination of lead in urine and whole blood by stable isotope dilution gas chromatography-mass spectrometry"., Clinical Chemistry, vol. 40, No. 8, pp. 1494-1502, (1994).

Alivisatos, A.P., et al., "Organization of "nanocrystal molecules" using DNA"., Nature, vol. 382, pp. 609-611, (1996).

Bannon, D.I., et al., "Graphite furnace atomic absorption spectroscopic measurement of blood lead in matrix-matched standards"., Clinical Chemistry, vol. 40, No. 9, pp. 1730-1734, (1994).

Berens, C., et al., "A tetracycline-binding RNA aptamer"., Bioorganic & Medicinal Chemistry, vol. 9, pp. 2549-2556, (2001).

Bowins, R.J., et al., "Electrothermal isotope dilution inductively coupled plasma mass spectrometry method for the determination of sub-ng $ml^{-1}$ levels of lead in human plasma"., Journal of Analytical Atomic Spectrometry, vol. 9, pp. 1233-1236, (1994).

Breaker, R.R., "DNA aptamers and DNA enzymes" Current Opinion in Chemical Biology, vol. 1, pp. 26-31, (1997).

Brust, M., et al., "Novel gold-dithiol nano-networks with non-metallic electronic properties"., Advanced Materials, vol. 7, No. 9, pp. 795-797, (1995).

Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).

Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).

Chartrand, P., et al., "Effect of structural modifications on the activity of the leadzyme"., Biochemistry, vol. 36, No. 11, pp. 3145-3150, (1997).

Chen, J., et al., "Synthesis from DNA of a molecule with the connectivity of a cube"., Nature, vol. 350, pp. 631-633, (1991).

Chen, C-T., et al., "A highly selective fluorescent chemosensor for lead ions"., J. Am. Chem. Soc., vol. 124, pp. 6246-6247, (2002).

Chinnapen, D.J.F., et al., "Hemin-stimulated docking of cytochrome c to a hemin—DNA aptamer complex"., Biochemistry, vol. 41, No. 16, pp. 5202-5212, (2002).

Dubois, L.H., et al., "Synthesis, structure, and properties of model organic surfaces"., Annu. Rev. Phys. Chem., vol. 43, pp. 437-463, (1992).

Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Granadillo, V.A., et al., "The influence of the blood levels of lead, aluminum and vanadium upon the arterial hypertension"., Clinica Chimica Acta, vol. 233, pp. 47-59, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hock, B., "Antibodies for immunosensors, A review"., Analytica Chimica Acta, vol. 347, pp. 177-186, (1997).

Hoogstraten, C.G., et al., "NMR solution structure of the lead-dependent ribozyme: Evidence for dynamics in RNA catalysis"., J. Mol. Biol., vol. 284, pp. 337-350, (1998).

Iqbal, S.S., et al., "A review of molecular recognition technologies for detection of biological threat agents"., Biosensors & Bioelectronics, vol. 15, pp. 549-578, (2000).

Jagner, D., et al., "Determination of lead in microliter amounts of whole blood by stripping potentiometry"., Electroanalysis, vol. 6, pp. 285-291, (1994).

Jin, R., et al., "What controls the melting properties of DNA-linked gold nanoparticle assemblies?"., J. Am. Chem. Soc., vol. 125, No. 6, pp. 1643-1654, (2003).

Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).

Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lebruska, L.L., "Selection and Characterization of an RNA Decoy for Transcription Factor NF-κB"., Biochemistry, vol. 38, No. 10, pp. 3168-3174, (1999).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lemieux, S., et al., "Modeling active RNA structures using the intersection of conformational space: application to the lead-activated ribozyme"., RNA, vol. 4, pp. 739-749, (1998).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "Highly dispersible molecular sieve carbon nanoparticles"., Chem. Mater., vol. 16, No. 22, pp. 4205-4207, (2004).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Marcus, A.H., et al., "Estimating the contribution of lead based paint to soil lead, dust lead, and childhood blood lead"., American Society for Testing and Materials Spec. STP 1226, pp. 12-23, (1995).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.

Qiao, H., et al., "Transferability of blood lead determinations by furnace atomic absorption spectrophotometry and continuum background correction"., Clinical Chemistry, vol. 41, No. 10, pp. 1451-1454, (1995).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Scott, W.G., "RNA catalysis"., Current Opinion in Structural Biology, vol. 8, pp. 720-726, (1998).

Seeman, N.C., et al., "Emulating biology: Building nanostructures from the bottom up"., Proc. Natl. Acad. Sci., vol. 99, suppl. 2, pp. 6451-6455, (2002).

Seeman, N.C., "DNA in a material world"., Nature, vol. 421, pp. 427-431, (2003).

Soukup, G.A., et al., "Engineering precision RNA molecular switches"., Proc. Natl. Acad. Sci. USA, vol. 96, pp. 3584-3589, (1999).

Srisawat, C., et al., "Sephadex-binding RNA ligands: rapid affinity purification of RNA from complex RNA mixtures"., Nucleic Acids Research, vol. 29, No. 2 e4, pp. 1-5, (2001).

Storhoff, J.J., et al., "Programmed materials synthesis with DNA"., Chem. Rev., vol. 99, No. 7, pp. 1849-1862, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp. 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Telting-Diaz, M., et al., "Mass-produced ionophore-based fluorescent microspheres for trace level determination of lead ions"., Analytical Chemistry, vol. 74, No. 20, pp. 5251-5256, (2002).

Tsien, R.Y., "Fluorescent and photochemical probes of dynamic biochemical signals inside living cells"., Fluorescent Chemosensors for Ion and Molecule Recognition, (ed. Czarnik, A.W.), chapter 9, pp. 130-146, American Chemical Society, (1993).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Whaley, S.R., et al., "Selection of peptides with semiconductor binding specificity for directed nanocrystal assembly"., Nature, vol. 405, pp. 665-668, (2000).

Wiegand, T.W., et al., "High-affinity oligonucleotide ligands to human IgE inhibit binding to Fc epsilon receptor I"., The Journal of Immunology, vol. 157, pp. 221-230, (1996).

Wittmann, C., et al.,"Microbial and Enzyme sensors for environmental monitoring"., Handbook of Biosensors and Electronic Noses: Medicine, Food, and the Environment, pp. 299-332, (1997).

Yan, H., et al., "DNA-Templated self-assembly of protein arrays and highly conductive nanowires"., Science, vol. 301, pp. 1882-1884, (2003).

International Search Report dated Nov. 21, 2005 for corresponding PCT application No. PCT/US2005/001060.

Supplemental International Search Report dated Jan. 10, 2006 for corresponding PCT application No. PCT/US2005/001060.

Liu, J., et al., "Size control, metal substitution, and catalytic application of cryptomelane nanomaterials prepared using cross-linking reagents"., Chem. Mater., vol. 16, No. 2, pp. 276-285, (2004).

Cake, K.M., et al., "Partition of circulating lead between serum and red cells is different for internal and external sources of lead"., American Journal of Industrial Medicine, vol. 29, pp. 440-445, (1996).

English Translation of Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).

International Search Report dated Jan. 15, 2003, for corresponding PCT application No. PCT/US01/20557.

Breaker et al., "A DNA Enzyme that Cleaves RNA," Chem. & Biol., 1994, pp. 223-229, vol. 1.

Chartrand et al., Biochem., 1997, pp. 3145-3150, vol. 36.

Faulhammer et al., "Characterization and Divalent Metal-ion Dependence in In Vitro Selected Deoxyribozymes Which Cleave DNA/RNA Chimeric Oligonucleotides," J. Mol. Biol., 1997, pp. 188-202, vol. 269.

Deo et al., "A Selective, Ratiometric Flourescent Sensor for $Pb^{2+}$," J. Am. Chem. Soc., 2000, pp. 174-175, vol. 122.
Doudna et al., The Chemical Repertoire of Natural Ribozymes, pp. 222-228, vol. 418.
Geyer et al., "Lanthanide Probes for a Phosphodiester-Cleaving, Lead-Dependent, DNAzyme," J. Mol. Biol., 1998, pp. 483-489, vol. 275.
Geyer et al., "Evidence for the Metal-Cofactor Independence of an RNA Phosphodiester-Cleaving DNA Enzyme," Chem. & Biol., 1997, pp. 579-593, vol. 4.
Hoogstraten et al., J. Mol. Biol., 1998, pp. 337-350, vol. 284.
Hoogstraten et al., J. Am. Chem. Soc., 2002, pp. 834-842, vol. 124.
Katahira et al., European J. Biochem., 1998, pp. 727-733, Vo. 255.
Khan et al., Nucl. Acid. Res., 1996, pp. 3568-3575, vol. 24.
Kim et al., J. Biochem., 1997, pp. 1062-1067, vol. 122.
Kozumi et al., Allosteric Selection of Ribozymes That Respond to the Second Messengers cGMP and cAMP, Nature Struct. Biol., 1999, pp. 1062-1071, vol. 6.
Legault et al., J. Mol. Biol., 1998, pp. 325-335, vol. 284.
Lemieux et al., RNA, 1998, pp. 739-749, vol. 4.
Li et al, "In vitro Selection and Characterization of a Highly Efficient Zn(II)-Dependent RNA-Cleaving Deoxyribozyme," Nucl. Acid. Res., 2000, pp. 481-488, vol. 28.
Liu et al., "A Fiber-Optic Evanescent Wave DNA Biosensor Based on Novel Molecular Beacons," Anal. Chem., pp. 5054-5059, vol. 71.
Mecklenburg et al., Anal. Chimica Acta, 1997, pp. 79-86, vol. 347.
Mullah et al., Tetrahedron Lett., 1997, pp. 5751-5754, vol. 38.
Nazarenko et al., Nucl. Acid. Res., 1997, pp. 2516-2521, vol. 25.
Omichi et al., "Effect of Substrate RNA Sequence on the Cleavage Reaction by a Short Ribozyme," Nucl. Acid Res., 1998, pp. 5655-5661, vol. 26.
Omichi et al., Biochem., 1997, pp. 3514-3521, vol. 36.
Ota et al., "Effects of Helical Structures Formed by the Binding Arms of DNAzymes and Their Substrates on Catalytic Activity," Nucl. Acid. Res., 1998, pp. 3385-3391, vol. 26.
Potyrailo et al., "Adapting Selected Nucleic Acid Ligands (Aptamers) to Biosensors," Anal. Chem., 1998, pp. 3419-3425, vol. 70.
Sabanayagam et al., "Oligonucleotide Immobilization on Micropatterned Streptavidin Surfaces," Nucl. Acid. Res., 2000, vol. 28, 4 pages.
Santoro et al., "Mechanism and Utility of an RNA-Cleaving DNA Enzyme," Biochem., 1998, pp. 13330-13342, vol. 37.
Santoro et al., "A General Purpose RNA-Cleaving DNA Enzyme," Proc. Natl. Acad. Sci. USA, 1997, pp. 4262-4266, vol. 94.
Scott, Current Opinion in Structural Biology, 1998, pp. 337-350, vol. 8.
Stojanovic et al., "Aptamer-Based Folding Fluorescent Sensor for Cocaine," J. Am. Chem. Soc., 2001, pp. 4928-4931, vol. 122.
Stojanovic et al., "Fluorescence Sensors Based on Aptamer Self-Assembly," J. Am. Chem. Soc., 2000, pp. 11547-11548, vol. 123.
Streicher et al., Nucl. Acid. Res., 1993, pp. 311-317, vol. 21.
Sugimoto et al., FEBS Lett., 1996, pp. 96-100, vol. 393.
Walter et al., "Folding of the Four-Way Junction of the Hairpin Ribozyme," Biochem., 1998, pp. 17629-17636, vol. 37.
Wedekind et al., Nature Structural Biology, 1999, pp. 261-268, vol. 6.
Williams et al., EMBO J., pp. 4551-4557, vol. 14.
Abstract of: Iwasaki, K., Mizota, T., Kenkyu Hokoku—Kanagawa-ken Kogyo Shikensho 1991, 62, 57.
Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).
International Search Report dated Aug. 31, 2004 for PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896.
Liu, J., et al., "Improving fluorescent DNAzyme biosensors by combining Inter- and Intramolecular quenchers"., Analytical Chemistry, vol. 75, No. 23, pp. 6666-6672, (2003).

Liu, J., et al., "Stimuli-responsive disassembly of nanoparticle aggregates for light-up colorimetric sensing"., Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells"., Cardiovascular research, vol. 35, pp. 522-528, (1997).
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).
Beyer, S., et al., "A modular DNA signal translator for the controlled release of a protein by an aptamer", Nucleic Acids Research, vol. 34, No. 5, pp. 1581-1587, (2006).
Frauendorf, C., et al., "Detection of small organic analytes by fluorescing molecular switches", Bioorganic & Medicinal Chemistry, vol. 9, pp. 2521-2524, (2001).
Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).
Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).
Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).
Product Description: Pall Corporation, "Immunochromatographic, lateral flow or strip tests development ideas", found at: http://www.pall.com/34445_4154.asp, 7 pages, (1998).
Liu, J., et al., "Fast colorimetric sensing of adenosine and cocaine based on a general sensor design involving aptamers and nanoparticles", Angew. Chem. Int. Ed., vol. 45, pp. 90-94, (2006).
Liu, J., et al., "A simple and sensitive "dipstick" test in serum based on lateral flow separation of aptamer-linked nanostructures", Angewandte Chemie International Edition, vol. 45, pp. 7955-7959, (2006).
Jiang, P. et al., "Fluorescent detection of zinc in biological systems: recent development on the design of chemosensors and biosensors", Coordination Chemistry Reviews, vol. 248, pp. 205-229, (2004).
Lim, M.H. et al., "Metal-based turn-on fluorescent probes for sensing nitric oxide", Accounts of Chemical Research, vol. 40, No. 1, pp. 41-51, (2007).
Yoon, S. et al., "Screening mercury levels in fish with a selective fluorescent chemosensor", Journal of the American Chemical Society, vol. 127, pp. 16030-16031, (2005).
Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).
He, Q. et al., "A selective fluorescent sensor for detecting lead in living cells", Journal of the American Chemical Society, vol. 128, pp. 9316-9317, (2006).
Zeng, L. et al., "A selective turn-on fluorescent sensor for imaging copper in living cells", Journal of the American Chemical Society, vol. 128, pp. 10-11, (2006).
Wegner, S.V. et al., "Design of an emission ratiometric biosensor from MerR family proteins: A sensitive and selective sensor for Hg2+", Journal of the American Chemical Society, vol. 129, pp. 3474-3475, (2007).
Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: a simple, selective, and sensitive fluorescent metal ion sensor", Angew. Chem. Int. Ed. England, vol. 34, No. 8, pp. 905-907, (1995).
Torrado, A. et al., "Exploiting polypeptide motifs for the design of selective Cu(II) ion chemosensors" Journal of the American Chemical Society, vol. 120, pp. 609-610, (1998).
Grandini, P. et al., "Exploiting the self-assembly strategy for the design of selective CuII ion chemosensors", Angew. Chem. Int. Ed, vol. 38, No. 20, pp. 3061-3064, (1999).
Klein, G. et al., "A fluorescent metal sensor based on macrocyclic chelation", Chem. Comm., pp. 561-562, (2001).
Zheng, Y. et al., "A new fluorescent chemosensor for copper ions based on tripeptide glycyl-histidyl-lysine (GHK)", Organic Letters, vol. 3, No. 21, pp. 3277-3280, (2001).
Boiocchi, M. et al., "A two-channel molecular dosimeter for the optical detection of copper(II)" Chem. Comm, pp. 1812-1813, (2003).
Zheng, Y. et al., "Peptidyl fluorescent chemosensors for the detection of divalent copper", Analytical Chemistry, vol. 75, No. 7, pp. 1706-1712, (2003).
Zheng, Y. et al., "Development of fluorescent film sensors for the detection of divalent copper", Journal of the American Chemical Society, vol. 125, pp. 2680-2686, (2003).
Roy, B.C. et al., "Synthesis of new, pyrene-containing metal-chelating lipids and sensing of cupric ions", Organic Letters, vol. 5, No. 1, pp. 11-14, (2003).
Kaur, S. et al., "Photoactive chemosensors 4: a Cu2+ protein cavity mimicking fluorescent chemosensor for selective Cu2+ recognition", Tetrahedron Letters, vol. 45, pp. 5081-5085, (2004).
Mei, Y. et al., "A selective and sensitive chemosensor for Cu2+ based on 8-hydroxyquinoline", Tetrahedron Letters, vol. 47, pp. 2447-2449, (2006).
Zhang, X-B. et al., "A highly selective fluorescent sensor for Cu2+ based on 2-(2'-hydroxyphenyl)benzoxazole in a poly(vinyl chloride) matrix", Analytica Chimica Acta, vol. 567, pp. 189-195, (2006).
Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).
Kim, S. H. et al., "Hg2+-selective off-on and Cu2+-selective on-off type fluoroionophore based upon cyclam", Organic Letters, vol. 8, No. 3, pp. 371-374, (2006).
White, B. R. et al., "Fluorescent peptide sensor for the selective detection of Cu2+", Talanta, vol. 71, pp. 2015-2020, (2007).
Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).
Dujols, V. et al., "A long-wavelength fluorescent chemodosimeter selective for Cu(II) ion in water", Journal of the American Chemical Society, vol. 119, pp. 7386-7387, (1997).
Yang, J-S. et al., "Cu2+-induced blue shift of the pyrene excimer emission: a new signal transduction mode of pyrene probes", Organic Letters, vol. 3, No. 6, pp. 889-892, (2001).
Kaur, S. et al., "Photoactive chemosensors 3: a unique case of fluorescence enhancement with Cu(II)", Chem. Comm., pp. 2840-2841, (2002).
Wu, Q. et al., "Catalytic signal amplification using a heck reaction. An example in the fluorescence sensing of Cu(II)", Journal of the American Chemical Society, vol. 126, pp. 14682-14683, (2004).
Royzen, M. et al., "Ratiometric displacement approach to Cu(II) sensing by fluorescence", Journal of the American Chemical Society, vol. 127, pp. 1612-1613, (2005).
Xu, Z. et al., "Ratiometric and selective fluorescent sensor for CuII based on internal charge transfer (ICT)", Organic Letters, vol. 7, No. 5, pp. 889-892, (2005).
Wen, Z-C. et al., "A highly selective charge transfer fluoroionophore for Cu2+", Chem. Commun., pp. 106-108, (2006).
Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of Cu2+ cation", Organic Letters, vol. 8, No. 15, pp. 3235-3238, (2006).
Navani, N.K. et al., "Nucleic acid aptamers and enzymes as sensors", Current Opinion in Chemical Biology, vol. 10, pp. 272-281, (2006).
Liu, J. et al., "A catalytic beacon sensor for uranium with parts-per-trillion sensitivity and millionfold selectivity", Proceedings of the National Academy of Science, vol. 104, No. 7, pp. 2056-2061, (2007).
Georgopoulos, P.G. et al., "Environmental copper: its dynamics and human exposure issues", Journal of Toxicology and Environmental Health, Part B, vol. 4, pp. 341-394, (2001).
Hertzberg, R.P. et al., "Cleavage of DNA with methidiumpropyl-EDTA-iron(II): reaction conditions and product analyses", Biochemistry, vol. 23, pp. 3934-3945, (1984).
Yazzie, M. et al., "Uranyl acetate causes DNA single strand breaks in vitro in the presence of ascorbate (Vitamin C)", Chem. Res. Toxicol., vol. 16, pp. 524-530, (2003).
Bolletta, F. et al., "A [rull (bipy)3]-[1,9-diamino-3,7-diazanonane-4,6-dione] two-component system as an efficient on-off luminescent chemosensor for Ni2+ and Cu2+ in water, based on an ET (energy transfer) mechanism", Journal of the Chemical Society, Dalton Transactions, pp. 1381-1385, (1999).
Carmi, N. et al., "Characterization of a DNA-cleaving deoxyribozyme", Bioorganic & Medicinal Chemistry, vol. 9, issue 10, pp. 2589-2600, (2001).
Liu, J. et al., "A DNAzyme catalytic beacon sensor for paramagnetic Cu2+ ions in aqueous solution with high sensitivity and selectivity", Journal of the American Chemical Society, 2 pages, (2007), ASAP Web Release Date: Jul. 24, 2007.
Tanaka, K. et al., "Programmable self-assembly of metal ions inside artificial DNA duplexes", Nature Nanotechnology, vol. 1, pp. 190-194, (2006).
Achenbach, J.C. et al., "DNAzymes: From creation in vitro to application in vivo", Current Pharmaceutical Biotechnology, vol. 5, pp. 321-336, (2004).
Balaji, T. et al., "Optical sensor for the visual detection of mercury using mesoporous silica anchoring porphyrin moiety", The Analyst, vol. 130, pp. 1162-1167, (2005).
Caballero, A. et al., "Highly selective chromogenic and redox or fluorescent sensors of Hg2+ in aqueous environment based on 1,4-disubstituted azines", Journal of the American Chemical Society, vol. 127, pp. 15666-15667, (2005).
Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).
Chen, P. et al., "A general strategy to convert the merR family proteins into highly sensitive and selective fluorescent biosensors for metal ions", Journal of the American Chemical Society, vol. 126, pp. 728-729, (2004).
Chiuman, W. et al., "Efficient signaling platforms built from a small catalytic DNA and doubly labeled fluorogenic substrates", Nucleic Acids Research, vol. 35, No. 2, pp. 401-405, (2007).
Cruz, R.P.G. et al., "Dinucleotide junction cleavage versatility of 8-17 deoxyribozyme", Chemistry & Biology, vol. 11, pp. 57-67, (2004).
Frasco, M.F. et al., "Mechanisms of cholinesterase inhibition by inorganic mercury", the FEBS Journal, vol. 274, pp. 1849-1861, (2007).
Guo, X. et al., "A highly selective and sensitive fluorescent chemosensor for Hg2+ in neutral buffer aqueous solution", The Jouranl of the American Chemical Society, vol. 126, pp. 2272-2273, (2004).
Harris, H.H. et al., "The chemical form of mercury in fish", Science, vol. 301, pp. 1203, (2003).
Ha-Thi, M-H. et al., "Highly selective and sensitive phosphane sulfide derivative for the detection of Hg2+ in an organoaqueous medium", Organic Letters, vol. 9, no. 6, pp. 1133-1136, (2007).
Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion (Hg2+) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "MercuryII-mediated formation of thymine-HgII-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "Highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic Hg2+-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, no. 21, pp. 5250-5257, (2000).

Tanaka, Y. et al., "15N-15N J-coupling across HgII: Direct observation of HgII-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized BR-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting Hg2+ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative Hg2+ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-bawsed fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).
Lee, J.F. et al., "Aptamer database", Nucleic Acids Research, vol. 32, Database Issue, pp. D95-D100, (2004).
Levy, M. et al., "Quantum-dot aptamer beacons for the detection of proteins", ChemBioChem, vol. 6, pp. 2163-2166, (2005).
Liu, J. et al., "Smart nanomaterials responsive to multiple chemical stimuli with controllable cooperativity", Advanced Materials, vol. 18, pp. 1667-1671, (2006).
Liu, J. et al., "Preparation of aptamer-linked gold nanoparticle purple aggregates for colorimetric sensing of analytes", Nature Protocols, vol. 1, No. 1, pp. 246-252, (2006).
Medintz, I.L. et al., "Quantum dot bioconjugates for imaging, labeling and sensing", Nature Materials, vol. 4, pp. 435-446, (2005).
Miduturu, C. V. et al., "Modulation of DNA constraints that control macromolecular folding", Angew. Chem. Int. Ed., vol. 45, pp. 1918-1921, (2006).
Mitchell, G.P. et al, "Programmed assembly of DNA functionalized quantum dots", Journal of the American Chemical Society, vol. 121, No. 35, pp. 8122-8123, (1999).
Nutiu, R. et al., "Structure-switching signaling aptamers: Transducing molecular recognition into fluorescence signaling", Chem. Eur. J., vol. 10, pp. 1868-1876, (2004).
Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).
Rajendran, M. et al., "In vitro selection of molecular beacons", Nucleic Acids Research, vol. 31, No. 19, pp. 5700-5713, (2003).
Vet, J.A.M. et al., "Multiplex detection of four pathogenic retroviruses using molecular beacons", Proceedings of the National Academy of Science, USA., vol. 96, pp. 6394-6399, (1999).
Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).
Wilson, R. et al., "Encoded microcarriers for high-throughput multiplexed detection", Angewandte Chemie International Edition, vol. 45, pp. 6104-6117, (2006).
Winkler, W.C. et al., "Regulation of bacterial gene expression by riboswitches", The Annual Review of Microbiology, vol. 59, pp. 487-517, (2005).
Yang, C.J. et al., "Light-switching excimer probes for rapid protein monitoring in complex biological fluids", PNAS, vol. 102, No. 48, pp. 17278-17283, (2005).
Liu, J. et al., "Quantum dot encoding of aptamer-linked nanostructures for one-pot simultaneous detection of multiple analytes", Analytical Chemistry, vol. 79, No. 11, pp. 4120-4125, (2007).
Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).
Allen, M.J. et al., "Magnetic resonance contrast agents for medical and molecular imaging", Met. Ions Biol. Syst., vol. 42, pp. 1-38, (2004).
Artemov, D. et al., "MR molecular imaging of the Her-2/neu receptor in breast cancer cells using targeted iron oxide nanoparticles", Magnetic Resonance in Medicine, vol. 49, pp. 403-408, (2003).
Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).
Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).
Carr, D.H. et al., "Gadolinium-DTPA as a contrast agent in MRI: initial clinical experience in 20 patients", American Journal of Roentfenol., vol. 143, pp. 215-224, (1984).
Chen, Y. et al., "An autonomous DNA nanomotor powered by a DNA enzyme", Angew. Chem. Int. Ed., vol. 43, pp. 3554-3557, (2004).
Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).
Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).
Drolet, D.W. et al., "An enzyme-linked oligonucleotide assay", Nature Biotechnology, vol. 14, pp. 1021-1025, (1996).
Enochs, W.S. et al., "Improved delineation of human brain tumors on MR images using a long-circulating, superparamagnetic iron oxide agent", Journal of Magnetic Resonance Imaging, vol. 9, pp. 228-232, (1999).
Famulok, M. et al., "Nucleic acid aptamers-from selection in vitro to applications in vivo", Accounts of Chemical research, vol. 33, No. 9, pp. 591-599, (2000).
Fang, X. et al., "Molecular aptamer for real-time oncoprotein platelet-derived growth factor monitoring by fluorescence anisotropy", Analytical Chemistry, vol. 73, No. 23, pp. 5752-5757, (2001).
Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).
Hamaguchi, N. et al., "Aptamer beacons for the direct detection of proteins", Analytical Biochemistry, vol. 294, pp. 126-131, (2001).
Harisinghani, M.G. et al., "Noninvasive detection of clinically occult lymph-node metastases in prostate cancer", The New England Journal of Medicine, vol. 348, No. 25, pp. 2491-2499, (2003).
Hermann, T. et al., "Adaptive recognition by nucleic acid aptamers", Science, vol. 287, pp. 820-825, (2000).
Hoppe-Seyler, F. et al., "Peptide aptamers: Specific inhibitors of protein function", Current Molecular Medicine, vol. 4, pp. 529-538, (2004).
Huang, C-C. et al., "Aptamer-modified gold nanoparticles for colorimetric determination of platelet-derived growth factors and their receptors", Analytical Chemistry, vol. 77, No. 17, pp. 5735-5741, (2005).
Josephson, L. et al., "High-efficiency intracellular magnetic labeling with novel superparamagnetic-tat peptide conjugates", Bioconjugate Chem., vol. 10, No. 2, pp. 186-191, (1999).
Josephson, L. et al., "The effects of iron oxides on proton relaxivity", Magnetic Resonance Imaging, vol. 6, pp. 647-653, (1988).
Josephson, L. et al., "Magnetic nanosensors for the detection of oligonucleotide sequences", Angew. Chem. Int. Ed., vol. 40, No. 17, pp. 3204-3206, (2001).
Kabalka, G. et al., "Gadolinium-labeled liposomes: Targeted MR contrast agents for the liver and spleen", Radiology, vol. 163, pp. 255-258, (1987).
Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).
Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).
Lee, J. et al., "A steroid-conjugated contrast agent for magnetic resonance imaging of cell signaling", Journal of American Chemical Society, vol. 127, No. 38, pp. 13164-13166, (2005).
Lewin, M. et al., "Tat peptide-derivatized magnetic nanoparticles allow in vivo tracking and recovery of progenitor cells", Nature Biotechnology, vol. 18, pp. 410-414, (2000).
Li, J.J. et al., "Molecular aptamer beacons for real-time protein recognition", Biochemical and Biophysical Research Communications, vol. 292, No. 1, pp. 31-40, (2002).
Li, W-H. et al., "A calcium-sensitive magnetic resonance imaging contrast agent", Journal of the American Chemical Society, vol. 121, No. 6, pp. 1413-1414, (1999).
Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat# inhibits transactivation and induces apoptosis in tumor cells", Molecular Cancer Research, vol. 2, pp. 170-182, (2004).

Nitin, N. et al., "Functionalization and pepride=based delivery of magnetic nanoparticles as an intracellular MRI contrast agent", J. Biol. lnorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relasometric and magnetic characterization of ultrasmall iron oxide nanoparticles with high magnetization. Evaluation as potential T1 magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric Cu2+ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., "Supporting Information for Colorimetric Cu2+ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucletides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for in Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Lupoid, S.E. et al., "Identification and characterization of nuclease-stabilized RNA molecules that bind human prostate cancer cells via the prostate-specific membrane antigen", Cancer Research, vol. 62, pp. 4029-4033, (2002).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.G. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).

Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).

Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).

Park, J.W. et al., "Development of Anti-P185$^{HER2}$ Immunoliposomes for Cancer-Therapy", Proceedings of the National Academy of Science U.S.A., vol. 92, pp. 1327-1331, (1995).

Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).

Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).

Gillies, E.R. et al., "A new approach towards acid sensitive copolymer micelles for drug delivery", Chemical Communications, Issue 14, pp. 1640-1641, (2003).

Joensuu, O.I., "Fossil Fuels as a Source of Mercury Pollution", Science, vol. 172, No. 3987, pp. 1027-1028, (1971).

Malm, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3, pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+-DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant -Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem. , vol. 15, pp. 1125-1136, (2004).

Boomer, D. W., et al, "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal. Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30 ° C", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants (pKa) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(ll)", Analytical Chemistry, vol. 68, No. 5, pp. 758-762, (1996).

Tabata, M. et al., "Chemical properties of water-miscible solvents separated by salting-out and their application to solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).
Deng, Z. et al., "DNA-Encoded self-assembly of gold nanoparticles into one-dimensional arrays", Angew. Chem. Int. Ed., vol. 44, pp. 3582-3585, (2005).
Zhao, W. et al., "Simple and rapid colorimetric biosensors based on DNA aptamer and noncrosslinking gold naoparticle aggregation", ChemBioChem, vol. 8, pp. 727-731, (2007).
Zhao, W. et al., "Highly stabilized nucleotide-capped small gold nanoparticles with tunable size", Advanced Materials, vol. 19, pp. 1766-1771, (2007).
Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).
Zhao, W. et al., "DNA aptamer folding on gold nanoparticles: from colloid chemistry to bionsenors", J. Am. Chem. Soc., vol. 130, (11), pp. 3610-3618, (2008).
Zhou, P. et al., "Extraction of oxidized and reduced forms of uranium from contaminated soils: effects of carbonate concentration pH", Environmental Science Technology, vol. 39, No. 12, pp. 4435-4440, (2005).
Jacoby, M., "Sensitive, selective mercury sensor nanoparticle-based colorimetric method detects part-per-billion levels of mercury", Chemical & Engineering News, pp. 1-3, May 2, 2007.
Cruz, R.P.G. et al., supplemental to "Dinucleotide junction cleavage versatility of 8-17 deoxyribozyme", Chemistry & Biology, vol. 11, pp. 57-67, (pp. 1-8) (2004).
Saleh, O. A. et al., "Direct detection of antibody-antigen binding using an on-chip artificial pore", Proceedings of the National Academy of Science, vol. 100, No. 3, pp. 820-824, (2003).
Han, C. et al., "Highly selective and sensitive colorimetric probes for Yb3+ ions based on supramolecular aggregates assembled from B-cyclodextrin-4,4'-dipyridine inclusion complex modified silver nanoparticles", Chem. Commun., pp. 3545-3547, (2009).
Aldaye, F.A., et al., "Sequential Self-Assembly of a DNA Hexagon as a Template for the Organization of Gold Nanoparticles", Angew. Chem. Int. Ed., 45, pp. 2204-2209, 2006.
Loweth, C.J. et al., "DNA-Based Assembly of Gold Nanocrystals", Angew. Chem. Int. Ed., 38, No. 12, pp. 1808-1812, 1999.
Carbone, A., et al., "Circuits and programmable self-assembling DNA structures", Proceedings of the National Academy of Sciences of the United States of America, vol. 99, No. 20, pp. 12577-12582, 2002.
Chelyapov, N., et al., "DNA Triangles and Self-Assembled Hexagonal Tilings", J. Am. Chem. Soc., 126, pp. 13924-13925, 2004.
Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, 1991.
Ding, B., et al., "Pseudohexagonal 2D DNA Crystals from Double Crossover Cohesion", J. Am. Chem. Soc., 126, pp. 10230-10231, 2004.
Endo, M., et al., "DNA Tube Structures Controlled by a Four-Way-Branched DNA Connector", Angew. Chem. Int. Ed., 44, pp. 6074-6077, 2005.
Fidanza, J.A, et al. "Site-Specific Labeling of DNA Sequences Containing Phosphorothioate Diesters", J. Am. Chem. Soc., 114, pp. 5509-5517, 1992.
Goodman, R.P., et al., "Rapid Chiral Assembly of Rigid DNA Building Blocks for Molecular Nanofabrication", Science, 310, pp. 1661-1665, 2005.
Hagleitner, C., et al., "Smart single-chip gas sensor microsystem", Nature, vol. 414, pp. 293-296, 2001.
He, Y., et al., "Sequence Symmetry as a Tool for Designing DNA Nanostructures", Angew. Chem. Int. Ed., 44, pp. 6694-6696, 2005.
Heath, J.R., et al., "A Defect-Tolerant Computer Architecture: Opportunities for Nanotechnology", Science, vol. 280, pp. 1716-1719, 1998.
Holloway, G., et al., "An Organometallic Route to Oligonucleotides Containing Phosphoroselenoate", ChemBioChem, 3, pp. 1061-1065, 2002.
Li, H., et al., "DNA-Templated Self-Assembly of Protein and Nanoparticle Linear Arrays", J. Am. Chem. Soc., 126, pp. 418-419, 2004.
Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, 1998.
Luduena, R.F., et al., N,N-Bis($\alpha$-iodoacetyl)-2,2'-dithiobis(ethylamine), a Reversible Crosslinking Reagent for Protein Sulfhydryl Groups, Analytical Biochemistry, 117. pp. 76-80, 1981.
Lund, K., et al., "Self-Assembling a Molecular Pegboard", J. Am. Chem. Soc., 127, pp. 17606-17607, 2005.
Mathieu, F., et al. "Six-Helix Bundles Designed from DNA", Nano Letters, vol. 5, No. 4, pp. 661-665, 2005.
Liu, H., et al, "Approaching the Limit: Can One DNA Oligonucleotide Assemble into Large Nanostructures?", Angew. Chem., 118, pp. 1976-1979, 2006.
Fidanza, J. et al, "Introduction of Reporter Groups at Specific Sites in DNA Containing Phosphorothioate Diesters", J. Am. Chem. Soc., 111, pp. 9117-9119, 1989.
Nakao, H., et al, "Highly Ordered Assemblies of Au Nanoparticles Organized on DNA", Nano Letters, vol. 3, No. 10, pp. 1391-1394, 2003.
Patolsky, F., et al., "Au-Nanoparticle Nanowires Based on DNA and Polylysine Templates", Angew. Chem. Int. Ed., 41, No. 13, pp. 2323-2327, 2002.
Pinto, Y., et al., "Sequence-Encoded Self-Assembly of Multiple-Nanocomponent Arrays by 2D DNA Scaffolding", Nano Letters, vol. 5, No. 12, pp. 2399-2402, 2005.
Rothemund, P., "Folding DNA to create nanoscale shapes and patterns", Nature, vol. 440, pp. 297-302, 2006.
Yang, X., et al, "Ligation of DNA Triangles Containing Double Crossover Molecules", J. Am. Chem. Soc., 120, pp. 9779-9786, 1998.
Seeman, N.C., "Nucleic Acid Nanostructures and Topology", Angew. Chem. Int. Ed., 37, pp. 3220-3238, 1998.
Seeman, N. C., "At the Crossroads of Chemistry, Biology, and Materials: Structural DNA Nanotechnology", Chemistry & Biology, vol. 10, pp. 1151-1159, 2003.
Le, J.D., et al., "DNA-Templated Self-Assembly of Metallic Nanocomponent Arrays on a Surface", Nano Letters, vol. 4, No. 12, pp. 2343-2347, 2004.
Seeman, N.C., et al. "Nucleic acid nanostructures: bottom-up control of geometry on the nanoscale", Reports on Progress in Physics, 68, pp. 237-270, 2005.
Warner, M.G., et al., "Linear assemblies of nanoparticles electrostatically organized on DNA scaffolds", Nature Materials, vol. 2, pp. 272-277, 2003.
Winfree, E., et al., "Design and self-assembly of two-dimensional DNA crystals", Nature, vol. 394, pp. 539-544, 1998.
Woehrle, G.H., et al., "Molecular-Level Control of Feature Separation in One-Dimensional Nanostructure Assemblies Formed by Biomolecular Nanolithography", Langmuir, 20, pp. 5982-5988, 2004.
Zhang, J., et al, "Periodic Square-Like Gold Nanoparticle Arrays Templated by Self-Assembled 2D DNA Nanogrids on a Surface", Nano Letters, vol. 6, No. 2, pp. 248-251, 2006.
Yang, T. et al. "Tunneling Phase Logic Cellular Nonlinear Networks", International Journal of Bifurcation and Chaos, vol. 11, No. 12, pp. 2895-2911, 2001.
Liu, Z., et al., "Imaging DNA Molecules on Mica Surface by Atomic Force Microscopy in Air and in Liquid", Microscopy Research and Technique, 66, pp. 179-185, 2005.
Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, 1998.

\* cited by examiner

Zn-DNA

5'- CTGCAGAATTCTAATACGACTCACTATAGGAAGAGATGGCGAC

Class I (used for reselection)
5,6,7,9,21,25,29,43,47
    ATCTC TTTTGTCAGCGACTCGAAATAGTGTGTTGAAGCAGCTCTA GTGAC

Class II
2,10,17,20,24,31,37,39
    AGCCA -TAGTTCTACCAGCGGTTCGAAATAGTGAAGTGTTCGTGA CTATC
3    GGCCA -TAGTTCTACCAGCGGTTCGAAATAGTGAAATGTTCGTGA CTATC
4    GCCAGATTAGTTCTACCAGCGGTTCGAAATAGTGAAATGTTCGTGA CTATC

Class III
15,18,19,34,35,38,50
    ATCTC CAAAGATGCCAGCATGCTATTCTCCGAGCCGGTCGAAATA GTGAC
14  ATCTC CAAAGATGCCTGCATGCTATTCTCCGAGCCGGTCGAAATA GTGAC

Unclassified
36  ATCTC GTCTCCGAGCCGGTCGAAATAGTCAGGTGTTTCTATTCGG GTGAC
40  ATCAC CTTCTCCGAGCCGGTCGAAATAGTAGTTTTTAGTATATCT GTGAC
42  ATCTC AGGTGTTGGCTGCTCTCGCGGTGGCGAGAGGTAGGGTGAT GTGAC

GGTAAGCTTGGCAC-3'

FIG. 2

Co-DNA

5'-*CTGCAGAATTCTAATACGACGCACTATAGGAAGAGATGGCGAC*

Class I (used for reselection)
18,15,34
      *ATCTC* TTGTATTAGCTACACTGTTAGTGGATCGGGTCTAATCTCG ·*GTGAC*
1    *GTCTC* TTGTATTAGCTACACTGTTAGTGGATCGGGTCTAATCTCG *GTGAC*
25  *ATCTC* CTGTATTAGCTACACTGTTAGTGGATCGGGTCTAATCTCG *GTGAC*
16  *ATCTC* TTGTATTAGCTACACTGTTAGTGGGAACGTTATCAT-TCG *GTGAC*

Class II
2,4,7,23,26
      *ATCTC* TTGACCCAAGAAGGGGTGTCAATCTAATCCGT CAACCATG
8    *ATCTC* TTGACCCAAGAAGGGGTGTCAATCAAATCCGT CAACCATG
17  *ATCTC* TTGACCCAAGAAGGGGTGTCAATCTAATCCGTACAACCATG ACGGTAAG
27  *ATCTC* TTGACCCAAGAAGGGGTGTCAATCTAATCCGT CAAGGATG    CGGTAAG

Class III
5    *ATCTC* AGGTGTTGGCTGCTCCCGCGGTGGCGGGAGGTAGGGTGAT *GTGAC*
11  *ATCTC* AGGTGTTGGCATCTCCCGCGGTGGCGAGAGGTAGGGTGAT *GTGAC*
6    *ATCTC* AGGTGTTGGCTGCTCTCGCGGTGGCGAGAGGTAGGGTCAT *GTGAC*

Unclassified
21  *ATCTC* GCAGTCGAAGCTTCACTGTTAGTGCGGACGGGTAGACTTC *GTGAC*
29  *ATTTC* TTCTGAATCCTCAATGTTAGTGGACCTAGTCGTAGTCGAT *GTGAC*
12  *ATCTC* GGAGCCAGTTAGCATAATCTTCTGAATCCTCAATGTTAGT *GTGAC*
10  *ATCTC* GGTGTTGGCTGGATAGAGCCGGTAGGCCCTATCGTAGGGT *GTGAC*
1    *GTCTC* TTTTGTCCGCGACTCGAAATAGTGTGTTGAAGCAGCTCTA *GTGAC*
28  *AGCCA* TAGTTCTACCAGCGGTTCGAAATAGTGAAGTGTTCGTGACTATCG GTAA

*GGTAAGCTTGGCAC-3'*

FIG. 3

HYPOTHETICAL SAMPLE RESULT

NUCLEIC ACID ENZYME BIOSENSORS FOR IONS

CROSS REFERENCE TO RELATED APPLICATION

This application is a continuation application of U.S. application Ser. No. 10/702,676, filed Nov. 6, 2003 now U.S. Pat. No. 7,192,708 entitled "Nucleic Acid Enzyme Biosensors for Ions", which is a divisional of 09/605,558 filed on Jun. 27, 2000 (issued Mar. 16, 2004 as U.S. Pat. No. 6,706,474) entitled "Nucleic Acid Enzyme Biosensors for Ions".

FEDERALLY SPONSORED RESEARCH OR DEVELOPMENT

The U.S. Government may have rights in the present invention pursuant to the terms of grant number R29 GM53706 awarded by the National Institutes of Health.

BACKGROUND

Many metals pose a risk as environmental contaminants. A well-known example is lead. Low level lead exposure can lead to a number of adverse health effects, with as many as 9-25% of pre-school children presently at risk. The level of lead in the blood considered toxic is $\geq 10$ µg/dL (480 nM). Current methods for lead analysis, such as atomic absorption spectrometry, inductively coupled plasma mass spectrometry, and anodic stripping voltammetry, often require sophisticated equipment, sample pre-treatment, and skilled operators.

Simple, rapid, inexpensive, selective and sensitive methods that permit real time detection of $Pb^{2+}$ and other metal ions are very important in the fields of environmental monitoring, clinical toxicology, wastewater treatment, and industrial process monitoring. Furthermore, methods are needed for monitoring free or bioavailable, instead of total, metal ions in industrial and biological systems.

Fluorescence spectroscopy is a technique well suited for very small concentrations of analytes. Fluorescence provides significant signal amplification, since a single fluorophore can absorb and emit many photons, leading to strong signals even at very low concentrations. In addition, the fluorescence time-scale is fast enough to allow real-time monitoring of concentration fluctuations. The fluorescent properties only respond to changes related to the fluorophore, and therefore can be highly selective. Furthermore, fluorometers for uses in the field are commercially available. Fluorescent detection is also compatible with fiber-optic technology and well suited for in vivo imaging applications. Several fluorescence-related parameters can be assessed for the purpose of sensing, including fluorescence intensity, emission or excitation wavelength, fluorescence lifetime and anisotropy.

Many fluorescent chemosensors, including fluorophore-labeled organic chelators (Rurack, et al., 2000; Hennrich et al., 1999; Winkler et al., 1998; Oehme & Wolfbeis, 1997) and peptides (Walkup & Imperiali, 1996; Deo & Godwin, 2000; Pearce et al., 1998), have been developed for metal ion detection. These ion sensors are usually composed of an ion-binding motif and a fluorophore. Metal detection using these fluorescent chemosensors relies on the modulation of the fluorescent properties of the fluorophore by the metal-binding event. Detection limits on the level of micromolar and even nanomolar concentrations have been achieved for heavy metal ions including $Zn^{2+}$, $Cu^{2+}$, $Hg^{2+}$, $Cd^{2+}$ and $Ag^+$. The design and synthesis of a chemosensor that exhibits highly selective and sensitive binding of the metal ion of choice in aqueous solution is still a big challenge, although the metal binding and the fluorescent moieties of the sensor can be systematically varied to achieve desired properties.

Nucleic acid molecules have previously been adapted to sense the presence of nucleic acids and to detect gene mutations from inherited diseases or chemical damages. In recent years, the molecular recognition and catalytic function of nucleic acids have been extensively explored. This exploration has lead to the development of aptamers and nucleic acid enzymes.

Aptamers are single-stranded oligonucleotides derived from an in vitro evolution protocol called systematic evolution of ligands by exponential enrichment (SELEX). Nucleic acid aptamers have been isolated from random sequence pools and can selectively bind to non-nucleic acid targets, such as small organic molecules or proteins, with affinities as high as $10^{-14}$ M (Uphoff et al., 1996; Famulok 1999). Most aptamers undergo a conformational change when binding their cognate ligands. With this property, several DNA and RNA aptamers have been engineered to sense L-adenosine or thrombin through an internally labeled fluorescent reporter group (Jhaveri et al., 2000). Thus, the conformational change in the aptamer upon binding leads to a change in fluorescence.

Nucleic acid enzymes are nucleic acid molecules that catalyze a chemical reaction. In vitro selection of nucleic acid enzymes from a library of $10^{14}$-$10^{15}$ random nucleic acid sequences offers considerable opportunity for developing enzymes with desired characteristics (Breaker & Joyce, 1994; Breaker, 1997). Compared with combinatorial searches of chemo- and peptidyl-sensors, in vitro selection of DNA/RNA is capable of sampling a larger pool of sequences, amplifying the desired sequences by polymerase chain reactions (PCR), and introducing mutations to improve performance by mutagenic PCR.

Allosteric ribozymes (or aptazymes), which combine the features of both aptamer and catalytic RNA, also hold promises for sensing small molecules (Potyrailo et al., 1998; Koizumi et al., 1999; Robertson & Ellington, 1999, 2000). Their reactivity is modulated through the conformational changes caused by the binding of small organic molecules to an allosteric aptamer domain. Therefore, the signal of ligand binding can be transformed into a signal related to chemical reaction.

Divalent metal ions can be considered as a special class of cofactors controlling the activity of nucleic acid enzymes. The reaction rate of the nucleic acid enzymes depends on the type and concentration of the metal ion in solution. Several RNA and DNA enzymes obtained through in vitro selection are highly specific for $Cu^{2+}$, $Zn^{2+}$, and $Pb^{2+}$, with metal ion requirements on the level of micromolar concentrations (Breaker & Joyce, 1994; Pan & Uhlenbeck, 1992; Carmi et al., 1996; Pan et al., 1994; Cuenoud & Szotak, 1995; Li et al., 2000; Santoro et al., 2000).

BRIEF SUMMARY

The present invention uses nucleic acid enzymes as signal transducers for ion detection. Compared with fluorescent chemosensor and protein biosensors, nucleic acid-based sensors are more amenable to combinatorial search for sequences with desired metal specificity and affinity. In addition, DNA, in particular, is stable and can be readily synthesized. A wide range of fluorescent dyes can be easily introduced at specific sites to suit different needs. DNA-based biosensors can also be adapted for use with optical fiber and DNA-chip technology for applications such as in vivo imaging, in situ detection, and array sensing.

In one aspect, the present invention provides for specific and sensitive biosensors of ions. The biosensors are useful in methods of detecting the presence of an ion, particularly metal ions such as $Pb^{2+}$. In certain embodiments, the biosensors may be used to determine the concentration of a particular ion in a solution.

The biosensors of the present invention use nucleic acid enzymes that require the presence of specific ions for their activity. Enzymatic activity leads to hydrolytic cleavage of a substrate nucleic acid that may be part of the nucleic acid enzyme itself. The resulting cleavage product then may be detected indicating the presence of the ion.

In a preferred embodiment, the biosensor comprises a fluorophore and a quencher arranged in proximity such that prior to cleavage the fluorescence intensity is decreased by the quencher. However, upon cleavage, the fluorophore and quencher are separated leading to an increase in fluorescence intensity. In a further preferred embodiment, the biosensor contains an array of nucleic acid enzymes having a range of sensitivities and specificities to several different ions.

A "nucleic acid enzyme" is a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made up of ribonucleotides, deoxyribonucleotides, or a combination of ribo- and deoxyribonucleotides.

A "sample" may be any solution that may contain an ion (before or after pre-treatment). The sample may contain an unknown concentration of an ion. For example, the sample may be paint that is tested for lead content. The sample may be diluted yet still remain a sample. The sample may be obtained from the natural environment, such as a lake, pond, or ocean, an industrial environment, such as a pool or waste system, a research lab, common household, or a biological environment, such as blood. Of course, sample is not limited to the taking of an aliquot of solution but also includes the solution itself. For example, a biosensor may be placed into a body of water to measure for contaminants. In such instance, the sample may comprise the body of water or a particular area of the body of water. Alternatively, a solution may be flowed over the biosensor without an aliquot being taken. Furthermore, the sample may contain a solid or may be produced by dissolving a solid to produce a solution. For example, the solution may contain soil from weapon sites or chemical plants.

"Measuring the product of the nucleic acid enzymatic reaction" includes measuring the result of the production of a product by an enzyme. For example, in an embodiment where the substrate comprises a quencher and the enzyme comprises a fluorophore and cleavage of the substrate by the enzyme leads to dissociation of the product from the enzyme, "measuring the product" includes detecting the increase of fluorescence. Thus, one is measuring the product by detecting its inability to quench fluorescence.

"Contacting a nucleic acid enzyme with a sample" includes placing the sample and enzyme in proximity such that an ion in the sample could be used as a cofactor. "Contacting" includes such acts as pipetting a sample onto a solid support or into a tube or well containing the nucleic acid enzyme. Alternatively, the enzyme may be brought to the sample. For example, the enzyme may be placed into a stream to monitor for the presence of a contaminant.

BRIEF DESCRIPTION OF THE DRAWINGS

FIG. 2. (SEQ ID NOS 13-23, respectively, in order of appearance) Sequence classes of cloned Zn-DNA. The numbers on the left are the clone-numbers randomly assigned to the sequences during the cloning and sequencing process. The highly conserved sequences (Region-20 nt) are in bold. The covariant nucleotides are underlined. The 5'- and the 3'-primer binding sequences are shown in italic.

FIG. 3. (SEQ ID NOS 24-42, respectively, in order of appearance) Sequence classes of the cloned Co-DNA. The clone-numbers are listed on the left. The 5' and the 3' primer binding sequences are in italic.

FIG. 9. The fluorescence response rate (vfluo) of Rh-17EDS-Dy for different divalent metal ions. The "control" was measured without Pb(II) or transition metal ions.

FIG. 10. Dependence of $v_{fluo}$ on the concentration of $Pb^{2+}$ or $Co^{2+}$. The reaction was carried out in the presence of 50 mM NaCl in 50 mM HEPES (pH 7.5).

FIG. 11. DNA chips for ion sensing.

DETAILED DESCRIPTION

Figure 1A:
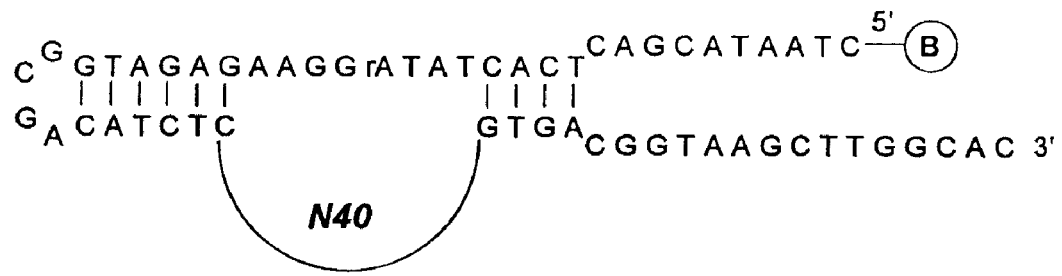
FIG. 1. Selection scheme for RNA-cleaving deoxyribozymes. (SEQ ID NO: 12) Starting pool of random-sequenced DNAs, engineered to contain two substrate-binding domains. Each member of the pool contains a 5'-terminal biotin (encircled B), a single embedded ribonucleotide (rA) and a 40-nucleotide random sequence domain (N40).
FIG. 1B. Selective amplification scheme for isolation of DNA that catalyzes the metal cofactor ($Co^{2+}$ or $Zn^{2+}$) dependent cleavage of an RNA phosphodiester.

The invention described herein represents a new class of ion sensors and is the first example of a DNA enzyme-based biosensor for ions. It combines the high selectivity of DNA enzymes with the high sensitivity of fluorescence detection. For example, in one embodiment, selectivity for $Pb^{2+}$ was >80 fold over other divalent metal ions with high sensitivity (>400% signal increase). Such selectivity and sensitivity provides for qualitative and quantitative detection of ions over a concentration range of several orders of magnitude. In a preferred embodiment, the fluorescence domain is decoupled from the ion-recognition/catalysis domain, and therefore the sensitivity and selectivity of this system may be manipulated by a careful choice of fluorophores and by performing in vitro selection of ion-binding domains to not only keep sequences reactive with the ion of choice, but also remove sequences that also respond to other ions.

In addition, DNA is stable, inexpensive and easily adaptable to optical fiber and chip technology for device manufacture. The attachment of DNA enzymes to optical fibers or chips allows regeneration of the sensors by washing away the cleavage products and adding new substrates. Finally, sequences specific for other ions and with various detection ranges may be isolated by varying the selection conditions, providing for a highly sensitive and selective fluorosensor system.

Nucleic Acid Enzymes

A growing number of nucleic acid enzymes have been discovered or developed showing a great diversity in catalytic activity (Table 1 and Table 2). Many if not all of the enzymes are dependent on one or more ion cofactors. In vitro selection may be used to "enhance" selectivity and sensitivity for a particular ion. Such enzymes find particular utility in the compositions and methods of the present invention. For example, nucleic acid enzymes that catalyze molecular association (ligation, phophorylation, and amide bond formation) or dissociation (cleavage or transfer) are particularly useful.

In preferred embodiments, a nucleic acid enzyme that catalyzes the cleavage of a nucleic acid in the presence of an ion is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available from, e.g., Biosearch, Inc. (Bedford, Mass.).

Ribozymes that may be used in the present invention include, but are not limited to, group I and group II introns, the RNA component of the bacterial ribonuclease P, hammerhead, hairpin, hepatitis delta virus and Neurospora VS ribozymes. Also included are in vitro selected ribozymes, such as those isolated by Tang and Breaker (2000).

One limitation of using a ribozyme is that they tend to be less stable than deoxyribozymes. Thus, in preferred embodiments, the nucleic acid enzyme is a deoxyribozyme. Preferred deoxyribozymes include those shown in FIG. 6A-6F and deoxyribozymes with extended chemical functionality (Santoro et al., 2000).

TABLE 1

Reactions catalyzed by ribozymes that were isolated from in vitro selection experiments.

| Reaction | $k_{cat}$ (min$^{-1}$) | $K_m$ (μM) | $k_{cat}/k_{uncat}$[a] | Reference |
|---|---|---|---|---|
| Phosphoester centers | | | | |
| Cleavage | 0.1 | 0.03 | $10^5$ | Vaish, 1998 |
| Transfer | 0.3 | 0.02 | $10^{13}$ | Tsang, 1996 |
| Ligation | 100 | 9 | $10^9$ | Ekland, 1995 |
| Phosphorylation | 0.3 | 40 | >$10^5$ | Lorsch, 1994 |
| Mononucleotide polymerization | 0.3 | 5000 | >$10^7$ | Ekland, 1996 |
| Carbon centers | | | | |
| Aminoacylation | 1 | 9000 | $10^6$ | Illangasekare, 1997 |
| Aminoacyl ester hydrolysis | 0.02 | 0.5 | 10 | Piccirilli, 1992 |
| Aminoacyl transfer | 0.2 | 0.05 | $10^3$ | Lohse, 1996 |
| N-alkylation | 0.6 | 1000 | $10^7$ | Wilson, 1995 |
| S-alkylation | $4 \times 10^{-3}$ | 370 | $10^3$ | Wecker, 1996 |
| Amide bond cleavage | $1 \times 10^{-5}$ | | $10^2$ | Dai, 1995 |
| Amide bond formation | 0.04 | 2 | $10^5$ | Wiegand, 1997 |
| Peptide bond formation | 0.05 | 200 | $10^6$ | Zhang, 1997 |
| Diels-Alder cycloaddition | >0.1 | >500 | $10^3$ | Tarasow, 1997 |
| Others | | | | |
| Biphenyl isomerization | $3 \times 10^{-5}$ | 500 | $10^2$ | Prudent, 1994 |
| Porphyrin metallation | 0.9 | 10 | $10^3$ | Conn, 1996 |

[a]Reactions catalyzed by ribozymes that were isolated from in vitro selection experiments. kcat/kuncat is the rate enhancement over uncatalyzed reaction.

TABLE 2

Deoxyribozymes isolated through in vitro selection.

| Reaction | Cofactor | $k_{max}$ (min$^{-1}$)[a] | $k_{cat}/k_{uncat}$ | Reference |
|---|---|---|---|---|
| RNA transesterification | $Pb^{2+}$ | 1 | $10^5$ | Breaker, 1994 |
| | $Mg^{2+}$ | 0.01 | $10^5$ | Breaker, 1995 |
| | $Ca^{2+}$ | 0.08 | $10^5$ | Faulhammer, 1997 |
| | $Mg^{2+}$ | 10 | >$10^5$ | Santoro, 1997 |
| | None | 0.01 | $10^8$ | Geyer, 1997 |
| | L-histidine | 0.2 | $10^6$ | Roth, 1998 |
| | $Zn^{2+}$ | ~40 | >$10^5$ | Li, J., 2000 |
| DNA cleavage | $Cu^{2+}$ | 0.2 | >$10^6$ | Carmi, 1996 |
| DNA ligation | $Cu^{2+}$ or $Zn^{2+}$ | 0.07 | $10^5$ | Cuenod, 1995 |
| DNA phosphorylation | $Ca^{2+}$ | 0.01 | $10^9$ | Li, Y., 1999 |
| 5',5'-pyrophophate formation | $Cu^{2+}$ | $5 \times 10^{-3}$ | >$10^{10}$ | Li, Y., 2000 |
| Porphyrin metalation | None | 1.3 | $10^3$ | Li, Y., 1996 |

[a]$k_{max}$ is the maximal rate constant obtained under optimized conditions.

An advantage of ribozymes and deoxyribozymes is that they may be produced and reproduced using biological enzymes and appropriate templates. However, the present invention is not limited to ribozymes and deoxyribozymes. Nucleic acid enzymes that are produced by chemical oligo-synthesis methods are also included. Thus, nucleic acids including nucleotides containing modified bases, phosphate, or sugars may be used in the compositions and methods of the present invention. Modified bases are well known in the art and include inosine, nebularine, 2-aminopurine riboside, $N^7$-denzaadenosine, and $O^6$-methylguanosine (Earnshaw & Gait, 1998). Modified sugars and phosphates are also well known and include 2'-deoxynucleoside, abasic, propyl, phosphorothioate, and 2'-O-allyl nucleoside (Earnshaw & Gait, 1998). DNA/RNA hybrids and PNAs may be used in the compositions and methods of the present invention. The stability of PNAs and relative resistance to cellular nucleases make PNA enzymes amenable to in vivo applications.

In certain embodiments, the substrate for the nucleic acid enzyme and the enzyme itself are contained in the same nucleic acid strand. Such enzymes are cis-acting enzymes. Examples include the $Zn^{2+}$-dependent deoxyribozymes (Zn-DNA) created in Example 1 (FIG. 1A and FIG. 2).

Figure 5:
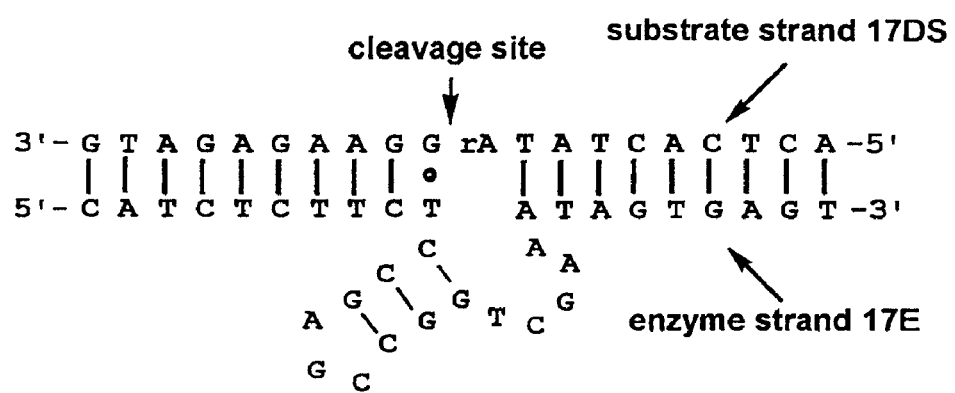

In preferred embodiments, the nucleic acid enzyme cleaves a nucleic acid strand that is separate from the strand comprising the enzyme (trans-acting). One advantage of utilizing trans-activity is that, after cleavage, the product is removed and additional substrate may be cleaved by the enzymatic strand. A preferred nucleic acid enzyme is 5'-CATCTCT-TCTCCGAGCCGGTCGAAATAGTGAGT-3' (17E; FIG. 5; SEQ ID NO:1). The corresponding preferred substrate to 17E is 5'-ACTCACTATrAGGAAGAGATG-3' (17DS; FIG. 5; SEQ ID NO:2), where rA denotes a single ribonucleotide.

It may be beneficial to use directed mutation to change one or more properties of a nucleic acid enzyme or its substrate. Using 17E and 17DS as an example, one may wish to alter the avidity of the two arms of the hybridized enzyme and substrate. The "arms" are those areas displaying Watson-Crick basepairing in FIG. 5. To alter avidity, one may increase or decrease the length of the arms. Increasing the length of the arms increases the number of Watson-Crick bonds, thus increasing the avidity. The opposite is true for decreasing the length of the arms. Decreasing the avidity of the arms facilitates the removal of substrate from the enzyme, thus allowing faster enzymatic turnover.

Another method of decreasing avidity includes creating mismatches between the enzyme and the substrate. Alternatively, the G-C content of the arms may be altered. Of course, the effect of any directed change should be monitored to ensure that the enzyme retains its desired activity, including ion sensitivity and selectivity. In light of the present disclosure, one of skill in the art would understand how to monitor for a desired enzymatic activity. For example, to ensure that the mutated enzyme maintained sensitivity and selectivity for $Pb^{2+}$, one would test to determine if the mutated enzyme remained reactive in the presence of lead (sensitivity) and maintained its lower level of activity in the presence of other ions (selectivity).

In preferred embodiments, the nucleic acid enzyme is sensitive and selective for a single ion. The ion may be any anion or cation. The ion may be monovalent, divalent, trivalent, or polyvalent. Examples of monovalent cations include $K^+$, $Na^+$, $Li^+$, $Tl^+$, $NH_4^+$, and $Ag^+$. Examples of divalent cations include $Mg^{2+}$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Hg^{2+}$, $Pt^{2+}$, $Ra^{2+}$, $Ba^{2+}$, and $Sr^{2+}$. Examples of trivalent cations include $Co^{3+}$, $Cr^{3+}$, and lanthanide ions ($Ln^{3+}$). Polyvalent cations include $Ce^{4+}$, spermine, and spermidine. Because, in certain embodiments, the biosensors of the present invention are used to monitor contaminants in the environment, preferred ions are those that are toxic to living organisms, e.g., $Ag^+$, $Pb^{2+}$ and $Hg^{2+}$.

Often the nucleic acid enzymes that have activity with one ion also have at least some activity with one or more other ions. Such multi-sensitive enzymes may still be used in the compositions and methods of the present invention. However, it should be understood that use of a multi-sensitive enzyme may lead to uncertainty as to which of the ions is present. In such cases, measuring the rate of enzymatic activity, using serial dilutions, or using an array of nucleic acid enzymes may be helpful in deciphering which ion is present.

In Vitro Selection of Nucleic Acid Enzymes

Many nucleic acid enzymes that are dependent on ions, particularly metal ions, for activity are known in the art (Breaker & Joyce, 1994; Pan & Uhlenbeck, 1992; Cuenoud & Szostak, 1995; Carmi et al., 1996; Li et al., 2000; Santoro et al., 2000). In light of the present disclosure, one of skill in the art would understand how to utilize a known nucleic acid enzyme in the methods and biosensors of the present invention. Furthermore, the present invention may include a nucleic acid enzyme created by in vitro selection. Methods of in vitro selection of nucleic acid enzymes are known in the art and described herein.

In vitro selection is a technique in which RNA or DNA molecules with certain functions are isolated from a large number of sequence variants through multiple cycles of selection and amplification (Joyce, 1994; Chapman et al., 1994). The concept of in vitro selection of catalytic RNA molecules was first introduced in the late 1980's. Since then, it has been widely applied to obtain ribozymes with maximized activities or novel catalytic abilities, and to identify oligonucleotides (called aptamers) that bind to certain proteins or small molecules with high affinity. The process for aptamers selection is sometimes referred as systematic evolution of ligands by exponential enrichment (SELEX) (Tuerk & Gold, 1990).

The first catalytic DNA (deoxyribozyme) was isolated by Breaker and Joyce in 1994 through in vitro selection. This deoxyribozyme is able to catalyze phosphodiester cleavage reaction in the presence of $Pb^{2+}$. Unlike RNA-based catalysts, DNA molecules with catalytic functions have not been encountered in nature, where DNA exists primarily as base-paired duplex and serves mainly as the carrier of genetic information. The identification of DNA molecules with catalytic functions further demonstrated the power of in vitro selection.

In vitro selection is typically initiated with a large collection of randomized sequences. A typical DNA or RNA library for selection contains $10^{13}$-$10^{16}$ sequence variants. The construction of a completely randomized pool is accomplished by chemical synthesis of a set of degenerated oligonucleotides using standard phosphoramidite chemistry. The 3'-phosphoramidite compounds of four nucleosides (A, C, G, and T) are premixed before being supplied to an automated DNA synthesizer to produce oligonucleotides. By controlling the ratio of four phosphoroamidites, the identity at each nucleotide position can be either completely random, i.e. with equal chance for each base, or biased toward a single base. Other strategies for creating a randomized DNA library include applying mutagenic polymerase chain reaction (PCR) and template-directed mutagenesis (Tsang and Joyce, 1996; Cadwell and Joyce, 1992, 1994). For the purpose of in vitro selection of functional RNA molecules, the randomized DNA library is converted to an RNA library through in vitro transcription.

In vitro selection takes advantage of a unique property of RNA and DNA, i.e., the same molecule can possess both genotype (coding information) and phenotype (encoded function). The DNA or RNA molecules in the randomized library are screened simultaneously. Those sequences that exhibit a desired function (phenotype) are separated from the inactive molecules. Usually the separation is performed through affinity column chromatography, being linked to or released from a solid support, gel electrophoresis separation, or selective amplification of a tagged reaction intermediate. The genotype of the active molecules are then copied and amplified, normally through polymerase chain reaction (PCR) for DNA or isothermal amplification reaction for RNA (Guatelli et al. 1990). Mutations can be performed with mutagenic PCR to reintroduce diversity to the evolving system. These three steps—selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA far beyond what has been found in nature. The selected ribozymes are capable of catalyzing a wide range of reactions at both phosphate and non-phosphate centers (Table 1). The reactions that are catalyzed by deoxyribozymes are less diverse, compared with the ribozymes (Table 2). However, the catalytic rate ($k_{cat}$) of most deoxyribozymes is comparable to that of the ribozymes catalyzing the same reaction. In certain cases, the catalytic efficiency ($k_{cat}/K_m$) of nucleic acid enzymes even exceeds that of the protein enzymes.

Figure 6A:
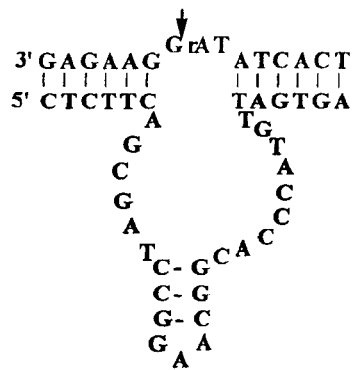
FIG. 6A (SEQ ID NOS 71 & 72) and FIG. 6B (SEQ ID NOS 73 & 74). The deoxyribozyme selected using $Mg^{2+}$ or $Pb^{2+}$ as cofactor (Breaker & Joyce, 1994, 1995).
Figure 6B:
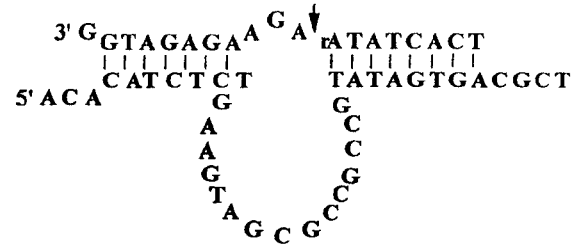
FIG. 6. Sequences and proposed secondary-structure of several RNA-cleaving deoxyribozymes.
FIG. 6C (SEQ ID NOS 75 & 76) and FIG. 6D (SEQ ID NOS 77 & 78). The 10-23 and the 8-17 deoxyribozymes selected in $Mg^{2+}$ to cleave all-RNA substrate (Santoro & Joyce, 1997).
FIG. 6E (SEQ ID NOS 79 & 80). The 17E deoxyribozyme selected in $Zn^{2+}$. In each structure, the upper strand is the substrate and the lower strand is the enzyme. Arrows identify the site of RNA transesterification.
Figure 6C:
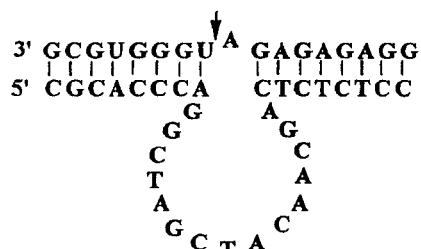
Figure 6D:
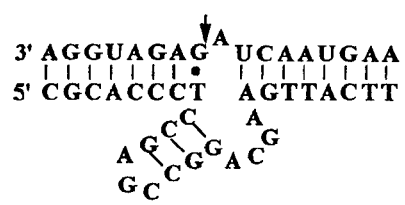
Figure 6E:
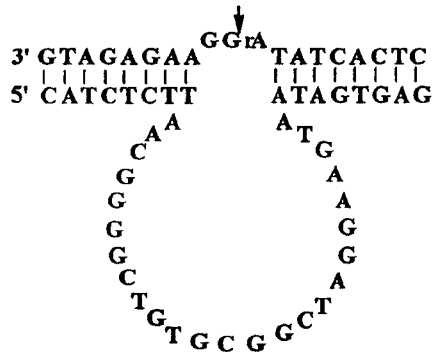
Figure 6F:
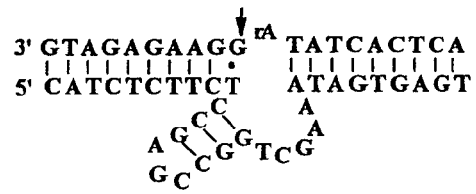

In vitro selection can be used to change the ion specificity or binding affinity of existing ribozymes, or to obtain nucleic acid enzymes specific for desired ions. For example, in vitro-selected variants of the group I intron (Lehman & Joyce, 1993) and the RNase P ribozyme (Frank & Pace, 1997) have greatly improved activity in $Ca^{2+}$, which is not an active metal ion cofactor for native ribozymes. The $Mg^{2+}$ concentration required for optimal hammerhead ribozyme activity has been lowered using in vitro selection to improve the enzyme performance under physiological conditions (Conaty et al., 1999; Zillman et al., 1997). Breaker and Joyce have isolated several RNA-cleaving deoxyribozymes using $Mg^{2+}$, $Mn^{2+}$, $Zn^{2+}$, or $Pb^{2+}$ as the cofactor (Breaker & Joyce, 1994, 1995). Only the sequence and structure of the $Pb^{2+}$-dependent and the $Mg^{2+}$-dependent deoxyribozymes were reported (FIGS. 6A and 6B). Other examples of metal-specific RNA/DNA enzymes obtained through in vitro selection include a $Pb^{2+}$-specific RNA-cleaving ribozyme (called leadzyme) (Pan & Uhlenbeck, 1992), a $Cu^{2+}$-specific DNA-cleaving deoxyribozyme (Carmi et al., 1996), and a DNA ligase active in $Zn^{2+}$ and $Cu^{2+}$ (Cuonod & Szostak, 1995).

Often nucleic acid enzymes developed for a specific metal ion by in vitro selection will have activity in the presence of other metal ions. For example, 17E deoxyribozyme was developed by in vitro selection for activity in the presence of $Zn^{2+}$. Surprisingly, the enzyme showed greater activity in the presence of $Pb^{2+}$ than $Zn^{2+}$. Thus, although produced in a process looking for $Zn^{2+}$-related activity, 17E may be used as a sensitive and selective sensor of $Pb^{2+}$.

To produce nucleic acid enzymes with greater selectivity, a negative selection step may be included in the process. For Example, $Pb^{2+}$-specific deoxyribozymes may be isolated using a similar selection scheme as for the selection of $Co^{2+}$- and $Zn^{2+}$-dependent DNA enzymes described in Example 1. In order to obtain deoxyribozymes with high specificity for $Pb^{2+}$, negative-selections may be carried out in addition to the positive selections in the presence of $Pb^{2+}$.

For negative selection, the DNA pool is selected against a "metal soup", which contains various divalent metal ions (e.g. $Mg^{2+}$, $Ca^{2+}$, $Mn^{2+}$, $Zn^{2+}$, $Cd^{2+}$, $Co^{2+}$, $Cu^{2+}$, etc.). Those sequences that undergo self-cleavage in the presence of divalent metal ions other than $Pb^{2+}$ are then washed off the column. The remaining sequences are further selected with $Pb^{2+}$ as the cofactor. $Pb^{2+}$-dependent deoxyribozymes with different affinities for $Pb^{2+}$ can be obtained by controlling the reaction stringency ($Pb^{2+}$ concentration).

Fluorophores and Quenchers

Any chemical reaction that leads to a fluorescent or chemiluminescent signal may be used in the compositions and methods of the present invention. In preferred embodiments, fluorophores are used to measure enzymatic activity and, thus, detect the presence of a particular ion. Essentially any fluorophore may be used, including BODIPY, fluoroscein, fluoroscein substitutes (Alexa Fluor dye, Oregon green dye), long wavelength dyes, and UV-excited fluorophores. These and additional fluorphores are listed in *Fluorescent and Luminescent Probes for Biological Activity, A Practical Guide to Technology for Quantitative Real-Time Analysis*, Second Ed. W. T. Mason, ed. Academic Press (1999) (incorporated herein by reference). In preferred embodiments, the fluorophore is 6-carboxytetramethylrhodamin (TAMRA). TAMRA has an excitation range of 500-550 nm and an emission range of 560-650 nm.

In certain embodiments, the substrate is labeled with a fluorophore and measurement of enzymatic activity is done by detecting the non-hybridized cleavage products in solution. Preferably, this is done by measuring the level of fluorescence in solution without detecting fluorescence from the bound substrate. This may be done by creating a flow such that, once the cleavage product enters the solution, it is carried away by the flow. Fluorescence of the flow is then measured in an area away from the enzyme-substrate pairs.

In preferred embodiments, the substrate is labeled with a fluorophore but fluorescence is quenched by a nearby quenching molecule. Quenching molecules absorb the energy of the excited fluorophore. Close proximity of fluorophore and quencher allow for the energy to be transferred from the fluorophore to the quencher. By absorbing this energy, the quencher prevents the fluorophore from releasing the energy in the form of a photon.

Quenchers may be categorized as non-fluorescent and fluorescent quenchers. Non-fluorescent quenchers are capable of quenching the fluorescence of a wide variety of fluorophores. Generally, non-fluorescent quenchers absorb energy from the fluorophore and release the energy as heat. Examples of non-fluorescent quenchers include DABCYL, QSY-7, and QSY-33.

Fluorescent quenchers tend to be specific to fluorophores that emit at a specific wavelength range. Fluorescent quenchers often involve fluorescence resonance energy transfer (FRET). In many instances the second molecule is also a fluorophore. In such cases, close proximity of the fluorophore and quencher is indicated by a decrease in fluorescence of the "fluorophore" and an increase in fluorescence in the fluorescent quencher. Commonly used fluorescent fluorophore pairs (fluorophore/fluorescent quencher) include fluorescein/tetramethylrhodamine, IAEDANS/fluorescein, fluorescein/fluorescein, and BODIPY FL/BODIPY FL.

Figure 8:
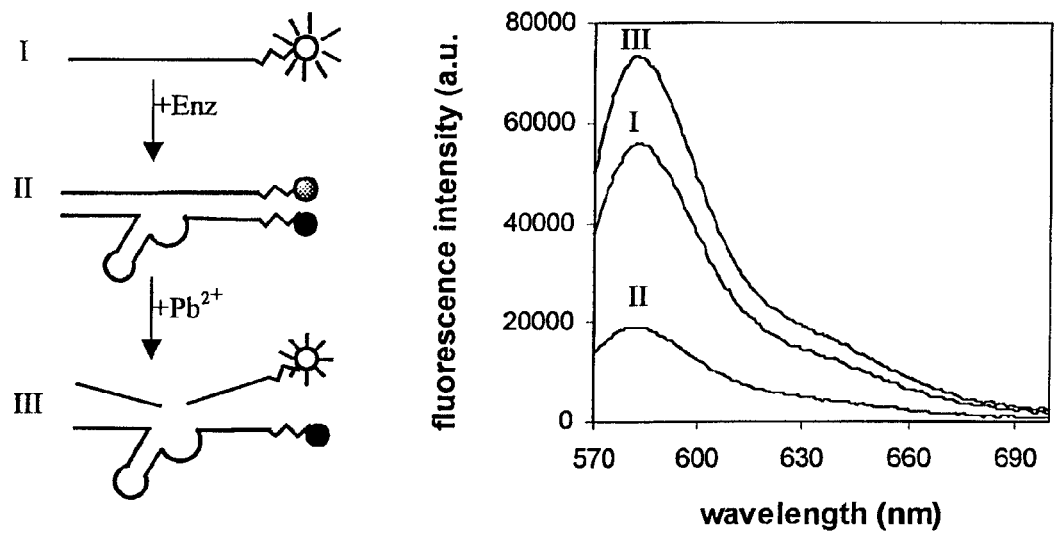
FIG. 8. Steady-state fluorescence spectra of the substrate (Rh-17DS) alone (I), after annealing to the deoxyribozyme (17E-Dy) (II), and 15 min after adding 500 nM Pb(OAc)$_2$ (III).

The quencher may be located on a support such that it is in proximity with the fluorophore when the substrate is bound to the enzyme. In preferred embodiments, the quencher is linked to the enzyme. Even more preferred is to have the fluorophore linked to the 5' end of the substrate and the quencher linked to the 3' end of the enzyme such that when the substrate and enzyme are hybridized, the fluorophore and the quencher are in close proximity to each other. Upon cleavage of the substrate, the product disassociates from the enzyme. Dissociation removes the fluorophore from the quencher, leading to an increase in fluorescence (FIG. 8).

Of course, it would be understood that the fluorophore could be linked essentially anywhere on the substrate and quencher essentially anywhere on the enzyme, as long as they are in close proximity to each other when the enzyme is hybridized to the substrate. By close proximity, it is meant that they are situated such that the quencher is able to function. Furthermore, the quencher may be placed on the substrate and the fluorophore on the enzyme. Alternatively, both quencher and fluorophore may be linked to the substrate on opposite ends from the potential cleavage site. Cleavage of such a molecule would lead to dissociation of the two ends and thus separation of the fluorophore and quencher, leading to an increase in fluorescence. Similarly, in embodiments wherein the enzyme and the substrate are contained within the same nucleic acid strand, the fluorophore and quencher may be placed on opposite ends of the cleavage site.

When choosing a fluorophore, quencher, or where to position the molecules, it is important to consider, and preferably to test, the effect of the fluorophore or quencher on the enzymatic activity of the nucleic acid enzyme. Also, it is preferable that the fluorophore display a high quantum yield and energy transfer efficiency. Long-wavelength (excitation and emission) fluorophores are preferred because of less interference from other absorbing species. The fluorophore should also be less sensitive to pH change or to non-specific quenching by metal ions or other species.

Methods and devices for detecting fluorescence are well developed. Essentially any instrument or method for detecting fluorescent emissions may be used. For example, WO 99/27351 (incorporated herein in its entirety) describes a monolithic bioelectronical device comprising a bioreporter and an optical application specific integrated circuit (OASIC). The device allows remote sampling for the presence of substances in solution.

Furthermore, the fluorescence may be measured by a number of different modes. Examples include fluorescence intensity, lifetime, and anisotropy in either steady state or kinetic rate change modes (Lakowicz, 1999).

Sometimes other factors in a solution such as pH salt concentration or ionic strength, or viscosity will have an effect on fluorescence. Others may affect the hybridization of the substrate and enzyme. Therefore, in preferred methods, controls are run to determine if the solution itself, regardless of enzymatic activity, is altering the fluorescence. Such controls include the use of non-cleavable substrates and or substrate without the presence of enzyme.

Biosensors

Described herein are nucleic acid enzymes that are dependent on the presence of a specific ion for activity. Using fluorophores or fluorophore/quencher labeling, it is possible to measure enzymatic activity, even in real time. These qualities make the compositions of the present invention excellent for use in biosensors for detecting ions.

Many biosensors utilizing nucleic acids are known in the art. For example, biosensors using aptamers have been developed for detecting molecules such as thrombin or adenosine (Potyrailo et al., 1999; Lee & Walt, 2000). In light of the present disclosure, one of ordinary skill in the art would know how to modify the nucleic acid biosensors to include nucleic acid enzymes.

In a simple embodiment, a biosensor of the present invention comprises a nucleic acid enzyme labeled with a quencher, a substrate labeled with a fluorophore, and a device to detect fluorescence such as a fluorescence microscope or a fluorometer. In a method using this embodiment, the enzyme and substrate are contacted with a sample suspected of containing an ion to which the enzyme is sensitive. Fluorescence is measured and compared to a control wherein the ion is absent. Change in fluorescence is indicative of the presence of the ion.

Of course, many variants of even this simple embodiment are included within the scope of the invention. Such variants include placing the enzyme, substrate, and sample in the well of a microtiter plate and measuring fluorescence with a microtiter plate reader. In another variation, the enzyme is attached to a solid support. When the enzyme is attached to a solid support, it is preferable that a linker is used. An exemplary linking system is biotin/streptavidin. For example, the biotin molecule may be linked to the enzyme and a plate may be coated with streptavidin. When linking an enzyme to a solid support, it is important to determine the effect of linkage on the enzymatic activity of the enzyme.

In an alternative embodiment, the solid support may be a bead and fluorescence measured using a flow cytometer. In embodiments having the enzyme attached to a solid support, the biosensor may be reusable. Old substrate and sample is removed, leaving the enzyme in place. New substrate and sample may then be added.

In another embodiment, the nucleic acid enzyme may be used in conjunction with fiber-optics (Lee & Walt, 2000). The nucleic acid enzyme may be immobilized on the surface of silica microspheres and distributed in microwells on the distal tip of an imaging fiber. The imaging fiber may then be coupled to a epifluorescence microscope system.

In certain embodiments, the biosensor will comprise an array of nucleic acid enzymes. The arrays of the present invention provide for the simultaneous screening of a variety of ion by nucleic acid enzymes. The array may contain as little as 2 or as many as 10,000 different nucleic acid enzymes. Of course, any integer in between may be used. Preferably, each individual nucleic acid enzyme has a measurable difference in specificity or affinity for at least one ion compared to at least one other nucleic acid enzyme within the array.

In preferred embodiments, the array is a high-density array like those used in DNA-chip technologies. Methods of forming high density arrays of nucleic acids with a minimal number of synthetic steps are known (U.S. Pat. No. 6,040,138). The nucleic acid array can be synthesized on a solid support by a variety of methods, including light-directed chemical coupling, and mechanically directed coupling (U.S. Pat. No. 5,143,854; WO 90/15070; WO 92/10092; WO 93/09668). Using this approach, one heterogenous array of polymers is converted, through simultaneous coupling at a number of reaction sites, into a different heterogenous array.

The light-directed combinatorial synthesis of nucleic acid arrays on a glass surface uses automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different nucleic acid analogues at different locations on the array is determined by the pattern of illumination during synthesis and the order of addition of coupling reagents.

In the event that a PNA is used in the procedure, it is generally inappropriate to use phosphoramidite chemistry to perform the synthetic steps, since the monomers do not attach to one another via a phosphate linkage. Instead, peptide synthetic methods are substituted (U.S. Pat. No. 5,143,854).

In addition to the foregoing, additional methods which can be used to generate an array of nucleic acids on a single solid support are known (For example, WO 93/09668). In these methods, reagents are delivered to the solid support by either (1) flowing within a channel defined on predefined regions or (2) "spotting" on predefined regions. However, other approaches, as well as combinations of spotting and flowing, may be employed. In each instance, certain activated regions of the solid support are mechanically separated from other regions when the monomer solutions are delivered to the various reaction sites.

A typical "flow channel" method applied to the nucleic acid enzyme arrays of the present invention can generally be described as follows. Diverse nucleic acid sequences are synthesized at selected regions of a solid support by forming flow channels on a surface of the solid support through which appropriate reagents flow or in which appropriate reagents are placed. For example, assume a monomer "A" is to be bound to the solid support in a first group of selected regions. If necessary, all or part of the surface of the solid support in all or a part of the selected regions is activated for binding by, for example, flowing appropriate reagents through all or some of the channels, or by washing the entire solid support with appropriate reagents. After placement of a channel block on the surface of the solid support, a reagent having the monomer A flows through or is placed in all or some of the channel(s). The channels provide fluid contact to the first selected regions, thereby binding the monomer A on the solid support directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the solid support; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the solid support at this stage of processing will be, for example, A, B, and AB. The process is repeated to form a vast array of nucleic acid enzymes of desired length and sequence at known locations on the solid support.

After the solid support is activated, monomer A can be flowed through some of the channels, monomer B can be flowed through other channels, a monomer C can be flowed through still other channels, etc. In this manner, many or all of the reaction regions are reacted with a monomer before the channel block must be moved or the solid support must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the solid support. For example, according to some embodiments, a protective coating such as a hydrophilic or hydrophobic coating (depending upon the nature of the solvent) is utilized over portions of the solid support to be protected, sometimes in combination with materials that facilitate wetting by the reactant solution in other regions. In this manner, the flowing solutions are further prevented from passing outside of their designated flow paths.

The "spotting" methods of preparing nucleic acid arrays can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire solid support surface can be sprayed or otherwise coated with a solution. In preferred embodiments, a dispenser moves from region to region, depositing only as much monomer as necessary at each stop. Typical dispensers include a micropipette to deliver the monomer solution to the solid support and a robotic system to control the position of the micropipette with respect to the solid support. In other embodiments, the dispenser includes a series of tubes, a manifold, an array of pipettes, or the like so that various reagents can be delivered to the reaction regions simultaneously.

Methods of detecting fluorescent signals on a DNA chip are well known to those of skill in the art. In a preferred embodiment, the nucleic acid enzyme array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

A confocal microscope may be automated with a computer-controlled stage to automatically scan the entire high density array. Similarly, the microscope may be equipped with a phototransducer (e.g., a photomultiplier, a solid state array, a ced camera, etc.) attached to an automated data acquisition system to automatically record the fluorescence signal produced by each nucleic acid enzyme on the array. Such automated systems are described at length in U.S. Pat. No. 5,143,854 and PCT application 20 92/10092.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain like or similar results without departing from the spirit and scope of the invention.

Example 1

In Vitro Selection of a Ion-Dependent Deoxyribozyme

This example demonstrates a method of creating nucleic acid enzymes that are dependent on the presence of an ion for activity. More specifically, use of a partially random DNA library to obtain deoxyribozymes that cleave RNA in the presence of $Zn^{2+}$ or $Co^{2+}$ is shown.

Materials and Methods Used in this Example

Oligonucleotides

DNA oligonucleotides were purchased from Integrated DNA Technologies Inc. Sequences of the random DNA template and the primers (P1, P2 and P3) used in PCR amplifications are listed below:

P1:
(SEQ ID NO:3)
5'-GTGCCAAGCTTACCG-3'

P2:
(SEQ ID NO:4)
5'-CTGCAGAATTCTAATACGACTCACTATAGGAAGAGATGGCGAC-3'

P3:
(SEQ ID NO:5)
5'-GGGACGAATTCTAATACGACTCACTATrA-3'

Template for Random DNA Pool:

(SEQ ID NO:6)
5'-GTGCCAAGCTTACCGTCAC-N40-GAGATCTCGCCATCTCTTCCTAT

AGTGAGTCGTATTAG-3'

Primer P1b and P3b are the 5'-biotinylated version of primers P1 and P3. Primer P1a and P3a were prepared by 5'-labeling P1 and P3 with [γ-$^{32}$P] ATP (Amersham) and T4 polynucleotide kinase (Gibco). The DNA/RNA chimeric substrate (17DS) for trans-cleavage assays has the sequence 5'-ACTCACTATrAGGAAGAGATG-3' (SEQ ID NO:2), where rA denotes a single ribonucleotide. The all-RNA substrate (17RS) with the same sequence was purchased from Dharmacon Research Inc. The trans-cleaving deoxyribozyme 17E has the sequence 5'-CATCTCTTCTCCGAGC-CGGTCGAAATAGTGAGT-3' (SEQ ID NO:1). The deoxyribozyme named 17E1 is a variant of 17E with the sequence 5'-CATCTCTTTTGTCAGCGACTCGAAATAGTGA GT-3' (SEQ ID NO:7). All oligonucleotides were purified using denaturing polyacrylamide gel electrophoresis and desalted with the SepPak nucleic acid purification cartridges (Waters) before use.

Preparation of Random DNA Pool

The initial pool for DNA selection was prepared by template-directed extension followed by PCR amplification. The extension was carried out with 200 pmol of DNA template containing a 40-nucleotide random sequence region, and 400 pmol of primer P3b in 20×100 µl reaction mixtures for four thermal-cycles (1 min at 92° C., 1 min at 52° C., and 1 min at 72° C.). Reaction buffer also included 0.05 U/µl Taq polymerase (Gibco), 1.5 mM $MgCl_2$, 50 mM KCl, 10 mM Tris-HCl (pH 8.3 at 25° C.), 0.01% gelatin and 0.2 mM of each dNTP. Subsequently, 1 nmol each of P1 and P3b were added to the extension product to allow four more cycles of PCR amplification. The products were precipitated with ethanol and dissolved in 0.5 ml of buffer A, which contains 50 mM HEPES (pH 7.0), 500 mM (for Zn-DNA selection) or 1 M (for Co-DNA selection) NaCl. About 20 µM EDTA was also added to the buffer to chelate trace amount of divalent metal ion contaminants.

In Vitro Selection

The random DNA pool was immobilized on a NeutrAvidin column (Pierce) by incubating with the column materials for 30 minutes. The mixture was gently vortex-mixed a few times during the incubation. The unbound DNA strands were eluted with at least 5×100 µl of buffer A. The non-biotinylated strands of immobilized DNA were washed off the column with 5×100 µl of freshly prepared 0.2 M NaOH and 20 µM EDTA. The column was then neutralized with 5×100 µl of buffer A. The cleavage reaction was carried out by incubating the immobilized single-stranded DNA containing the single ribonucleotide (rA) with 3×20 µl of reaction buffer (buffer A plus 1 mM $ZnCl_2$ or $CoCl_2$) over 1 h. The eluted DNA molecules were pooled and precipitated with ethanol. A fraction of the selected DNA was amplified in 100 µl PCR reaction with 40 pmol each of primers P1 and P2 over 10-20 thermal cycles. One tenth of the PCR product was further amplified for six cycles with 50 pmol of primers P1 and P3b. The final PCR product was ethanol precipitated and used to initiate the next round of selection. During the selection of Zn(II)-dependent deoxyribozymes (called Zn-DNA hereafter), the concentration of $ZnCl_2$ was kept constant at 100 µM in the reaction buffer for the following rounds of selection. Reaction time was gradually decreased from 1 h to 30 s within 12 rounds of selection. For the selection of Co(II)-dependent deoxyribozymes (called Co-DNA hereafter), the concentration of $CoCl_2$ was gradually decreased from 1 mM to 100 µM and the reaction time from 1 h to 1 min within 10 rounds of selection. The twelfth generation of selectively amplified Zn-DNA and the tenth generation of Co-DNA were cloned using TA-TOPO Cloning Kit (Invitrogen) and sequenced with T7 Sequenase 2.0 Quick-denatured Plasmid Sequencing Kit (Amersham).

Reselection

Based on the sequence of class I Zn-DNA or Co-DNA, partially degenerate DNA template libraries for reselection were synthesized (Integrated DNA Technology Inc.) with 20% degeneracy at the N40 region. In other words, during the oligonucleotide synthesis of the N40 region, the wild type sequence was introduced at a probability of 80% at each position, while the other three nucleotides each occurred at a probability of 6.67%. The reselection pool was prepared with 10 pmol of template and 100 pmol of primers P1 and P3b using the same protocol previously described. With 10 pmol (number of molecules $S=6\times10^{12}$) of partially randomized template, the statistic parameters of the DNA library used for reselection were calculated based on the following equations.

$$P(k,n,d)=[n!/(n-k)!k!]d^k(1-d)^{n-k} \qquad (1)$$

$$N(k)=[n!/(n-k)!k!]3^k \qquad (2)$$

$$C(n,k)=SP(k,n,d)/N(k) \qquad (3)$$

P(k,n,d) is the probability of having k mutations within n (number of randomized positions, n=40) nucleotide positions that have been randomized at a degeneracy of d. N(k) is the number of distinct sequences that have k mutations with respect to the prototype sequence. C(n,k) is the number of copies for each sequence that has k mutations. The reselection pool was expected to contain the wild type sequence, all possible sequences with 1-8 point mutations, and a sampling of the sequences with >8 point mutations. More than half of the population contains ≧8 point-mutations. The protocol for reselection was the same as the primary selection, except that the reaction time was decreased from 20 min to 1 min and the concentration of $ZnCl_2$ or $CoCl_2$ was decreased from 20 µM to 5 µM over six generations. The sixth generation of reselected Zn- or Co-DNA were cloned and sequenced as previously described.

Kinetic Assays of the Reselected Cis-Cleaving DNA

The 5' $^{32}$P-labeled precursor DNA for cis-cleavage assay was prepared by PCR-amplification of the selected DNA population or the cloned DNA plasmid with primer 1b and 3a. The double-stranded product was immobilized on a NeutrAvidin column through the biotin moiety on primer P1b. The catalytic strand of DNA was eluted off the column with 3×20 µl freshly prepared 0.2 N NaOH and neutralized with 8 µl of 3 M sodium acetate (pH 5.3) in the presence of 50 µg/ml bovine serum albumin (Sigma). Following ethanol precipitation, the single-stranded DNA was purified on an 8% denaturing polyacrylamide gel and desalted with SepPak nucleic acid purification cartridge. Bovine serum albumin (50 µg/ml) was added to the gel-soaking buffer (0.2 M NaCl, 20 µM EDTA, 10 mM Tris-HCl, pH 7.5) to prevent the DNA from adhering to the tube. The concentration of the DNA was determined by scintillation counting the radioactivity.

The precursor DNA was dissolved in buffer A and incubated at room temperature for 10 min before $CoCl_2$ or $ZnCl_2$ was added. The reaction was stopped with 50 mM EDTA, 90% formamide and 0.02% bromophenol blue. Reaction products were separated on an 8% denaturing polyacrylamide gel and quantified with a Molecular Dynamic phosphorimager.

In Vitro Selection of Zn(II)- or Co(II)-Dependent Deoxyribozymes

The DNA molecules capable of cleaving an RNA bond in the presence of $Co^{2+}$ or $Zn^{2+}$ were obtained through in vitro selection. The initial DNA library for selection contains ~$10^{14}$ out of the possible $10^{24}$ (=$4^{40}$) DNA sequences. These molecules consist of a random sequence domain of 40 nucleotides flanked by two conserved primer-binding regions. The sequence of the conserved region was designed in such a way that they could form two potential substrate-binding regions (FIG. 1A). A ribonucleic adenosine was embedded in the 5'-conserved sequence region and was intended to be the cleavage site, since an RNA bond is more susceptible than a DNA bond toward hydrolytic cleavage. The intrinsic half-life of the phosphodiester linkage in RNA at pH 7 and 25° C. is estimated to be 1,000 years. The corresponding value for DNA is 200 million years.

Figure 1B:
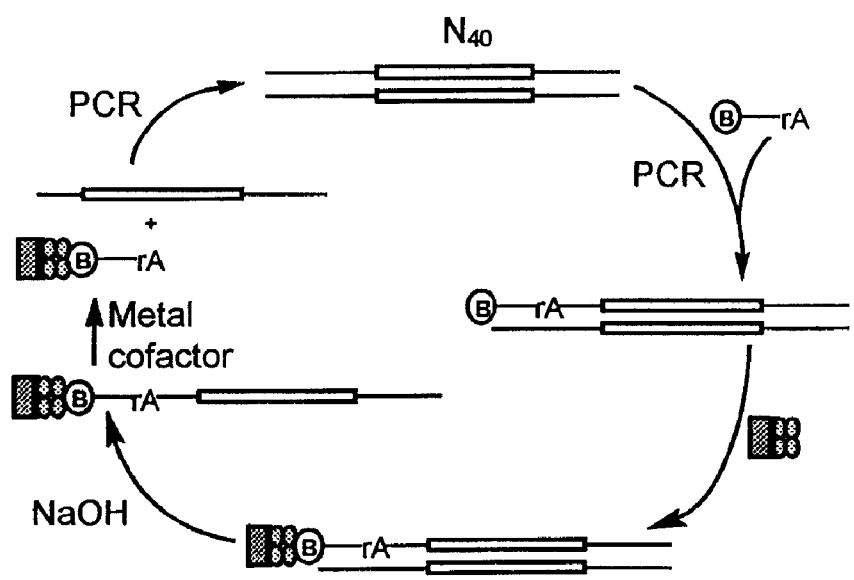

The DNA pool was immobilized on a NeutrAvidin column through the biotin moiety on the 5' terminus of the DNA. Biotin and Avidin bind strongly with an association constant of $K_a=10^{15}$ $M^{-1}$. The sequences that underwent self-cleavage in the presence of $Co^{2+}$ or $Zn^{2+}$ were eluted off the column, amplified and used to seed the next round of selection (FIG. 1B). The selection stringency was increased during the selection process with shorter reaction time and less available divalent metal ions. The activity of the selected Zn-DNA gradually increased until the twelfth generation and declined thereafter, while the highest activity was achieved with the tenth generation of Co-DNA. Therefore the twelfth generation of Zn-DNA and the tenth generation of Co-DNA were cloned and sequenced. The cloned sequences can be divided into different classes based on sequence similarity (FIG. 2 and FIG. 3).

Individual sequences of the cloned Zn-DNA and Co-DNA were randomly chosen and sampled for activity. Under the selection conditions (100 µM $Zn^{2+}$, 500 mM NaCl, 50 mM HEPES, pH 7.0 25° C.), the observed rate constants of Zn-DNAs from sequence-classes I and II were 0.1-0.2 $min^{-1}$, while class III sequences were less active, with $k_{obs}$ around 0.02 $min^{-1}$. Therefore, a $10^5$-$10^6$ fold increase in cleavage rate has been achieved for Zn-DNA selection. The cleavage rate of all the randomly picked Co-DNA sequences were <0.02 $min^{-1}$ under the conditions for Co-DNA selections (100 µM $Co^{2+}$, 1 M NaCl, 50 mM HEPES, pH 7.0 25° C.). Interestingly, even in the buffer (1 M NaCl, 50 mM HEPES, pH 7.0) alone, the class II Co-DNA exhibited similar activity as in the presence of 100 µM $Co^{2+}$ or $Zn^{2+}$.

Clone #5 of Zn-DNA (Zn-5) and clone #18 of Co-DNA (Co-18) showed relatively high activity, as well as high frequency of occurrence, within their lineages. The $k_{obs}$ were 0.17 $min^{-1}$ for Zn-5 (in 100 µM $Zn^{2+}$) and 0.02 $min^{-1}$ for Co-18 (in 100 µM $Co^{2+}$). The sequences of Zn-5 and Co-18 were partially randomized (see Material and Methods for details) and subjected to reselection in order to further improve the reactivity and metal-binding affinity, and to explore the sequence requirement of the conserved catalytic motif. Based on equations (1)-(3), the reselection pool was expected to contain the wild type sequence, all possible sequences with 1-8 point mutations, and a sampling of the sequences with >8 point mutations. More than half of the population should contain ≧8 point mutations. Six rounds of reselection were carried out with 5-20 µM $Zn^{2+}$ or $Co^{2+}$, however the activity of the reselected DNA was similar to the activity of the wild type sequences. Sequencing of the Zn-DNA from both the initial selection and reselection revealed a highly conserves sequence region. Therefore the lack of activity improvement after reselection likely reflects a sequence pool dominated by a few highly reactive sequences.

Sequence Alignment and Structure Analysis of Zn-DNA

The sequences of thirty individual clones of initially selected Zn-DNA can be divided into three major classes based on sequence similarity. Differences among members of each class were limited to a few point mutations (FIG. 2). A highly conserved sequence region of 20 nt, 5'-T$X_1X_2X_3$AGC$Y_1Y_2Y_3$TCGAAATAGT-3' (SEQ ID NO:8) (Region-20nt), was observed in all but one sequence albeit at different locations. The sequences of 5'-$X_1X_2X_3$-3' and 3'-$Y_3Y_2Y_1$-5' are complimentary and covariant, indicating that they form base pair with each other:

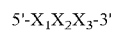

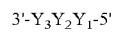

The secondary structures of the sequenced Zn-DNA were predicted using Zuker's DNA mfold program (see http://mfold.wustl.edu/~folder/dna/form1.cgi) through minimization of folding energy. The most stable structures predicted for those containing Region-20nt all contained a similar structure motif. This common motif consists of a pistol-shaped three-way helical junction formed by a 3 bp hairpin, an 8 bp hairpin and a double helix linking to the rest of the molecule. The 3 bp hairpin and its adjacent single-stranded regions are part of the Region-20nt. The ribonucleic adenosine is unpaired and positioned opposite of the 3 bp hairpin.

Figure 4:
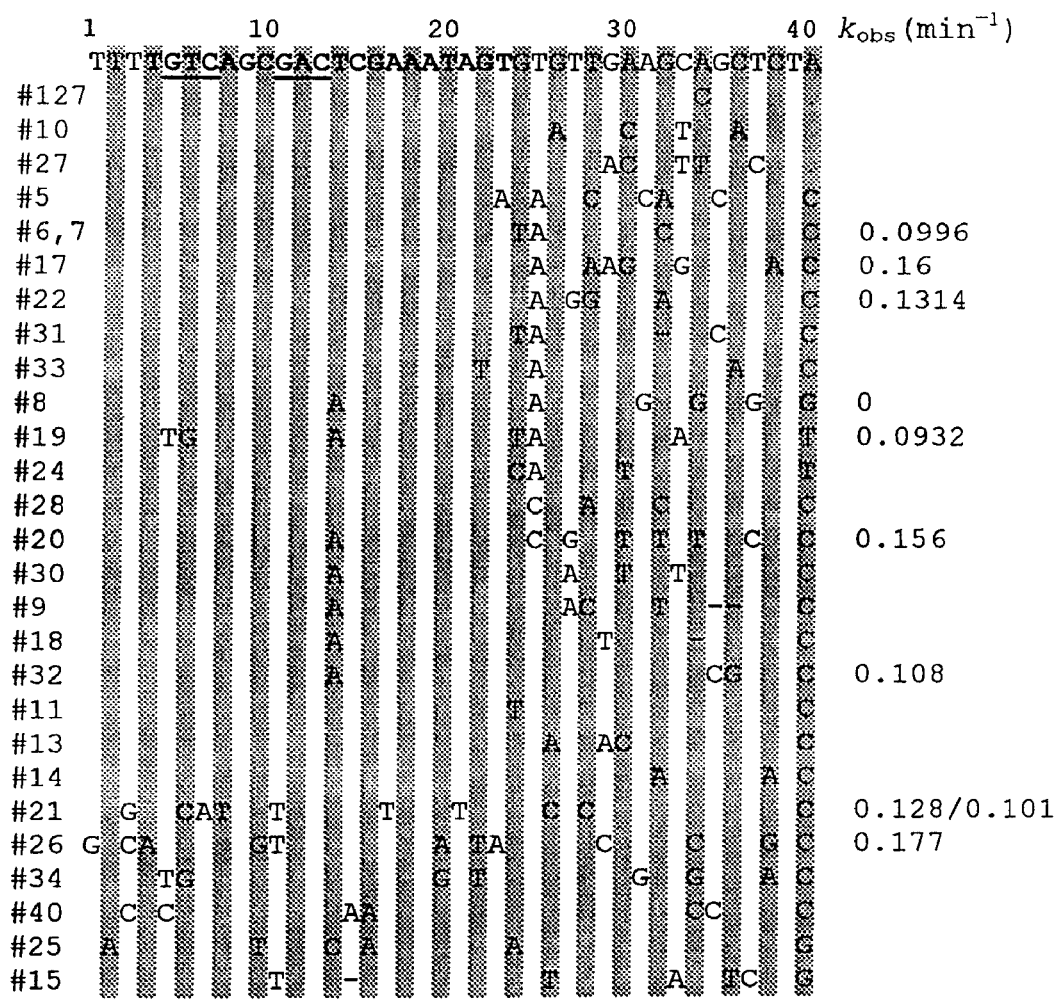
FIG. 4. (SEQ ID NOS 43-70, respectively, in order of appearance) Sequence alignment of the N40 region of the reselected Zn-DNAs. The wild-type sequence is listed on the top, followed by the reselected Zn-DNA sequences. Only the point mutations are shown for the reselected sequences, while the nucleotides that are identical to the wild type at the corresponding positions are omitted. Numbers listed on the left are clone-numbers. The rate constants ($k_{obs}$) of several reselected Zn-DNA in 100 μM $Zn^{2+}$ are shown on the right, FIG. 5. (SEQ ID NOS 1 & 2) Proposed secondary structure of the Zn(II)-dependent trans-cleaving deoxyribozyme.

After reselection, twenty-eight Zn-DNA clones were sequenced (FIG. 4). When compared with the parental wild type sequence (class I Zn-DNA), the reselected Zn-DNA contained point mutations mostly outside of Region-20nt. About one third of these sequences have a T→A mutation at position 73, converting the T-T mismatch in the wild type sequence to a Watson-Crick base pair. In one fourth of the reselected DNAs, the 5 nucleotide single-stranded bulge of the three-way junction has the sequence 5'-ACGAA-3', corresponding to 5'-TCGAA-3' in the wild type. Clone #17 (named ZnR17) of the reselected Zn-DNA is most active under selection conditions (FIG. 4). Structural analysis of ZnR17 revealed two completed base-paired helices in the three-way junction. Therefore, it was engineered into a trans-cleaving deoxyribozyme by deleting the sequences outside of the three-way junction and the loop of the 8 bp hairpin. Such truncation resulted in two individual stands, which hybridize with each other through two 9-10 bp helices. The strand containing the single ribonucleotide residue (rA) is considered as the substrate (named 17DS), while the other strand as the enzyme (named 17E). The catalytic core, which was highly conserved during selection, consists of a 3 bp hairpin and a 5 nt single-stranded bulge (FIG. 5).

Although ZnR17 was selected in $Zn^{2+}$, it does not contain structure motifs that were discovered in several Zn(II)-binding RNA molecules (Ciesiolka et al., 1995; Ciesiolka & Yarus, 1996). However, the conserved region of ZnR17 is very similar to that of the 8-17 deoxyribozymes selected by Santoro and Joyce using $Mg^{2+}$ as cofactor (Santoro & Joyce, 1997). The unpaired bulge region in the 8-17 DNA enzyme has the sequence 5'-WCGR-3' or 5'-WCGAA-3' (W=A or T; R=A or G). The highest activity was observed with the sequence containing 5'-TCGAA-3'. Among the Zn(II)-dependent deoxyribozymes we obtained after reselection, 85% of them fell within the 5'-WCGAA-3' regime (W=A or T). However, the sequence of the two double helices flanking the catalytic core is different between the 8-17 (FIG. 6D) and the 17E deoxyribozymes (FIG. 6F), reflecting their different designs of the selection pool. Similar sequence motif was also observed in an RNA-cleaving deoxyribozyme (named Mg5) selected by Faulhammer and Famulok using 50 mM histidine and 0.5 mM $Mg^{2+}$ as cofactors (Faulhammer & Famulok, 1997). The homologous region in 31 out of the 44 sequenced clones had the sequence 5'-$TX_1X_2X_3AGCY_1Y_2Y_3ACGAA$-3' (SEQ ID NO:9), falling within the WCGAA-3' regime. The authors predicted a secondary structure different from the 8-17 or 17E motif based on chemical modification analysis. However, a structure containing a three-way junction similar to that of the 17E and 8-17 deoxyribozymes is consistent with the chemical mapping results.

Sequence Alignment and Structure Analysis of Co-DNA

The sequences of the cis-cleaving deoxyribozyme selected in the presence of $Co^{2+}$ are more diverse than the Zn-DNA. They can be divided into three major classes based on sequence similarity (FIG. 3). There is no consensus sequence region among different classes. The secondary structure of each sequence class of Co-DNA was predicted with DNA mfold program. The minimal conserved sequence motif of class I Co-DNA includes a bulged duplex. The cleavage site is within the 13 nt single-stranded bulge. A 4 bp hairpin is also highly conserved and linked to the bulged duplex through 3 unpaired nucleotides. The folding of the sequences outside of this minimal motif was highly variable and resulted in structures with a wide range of stabilization energy.

Figure 7A:
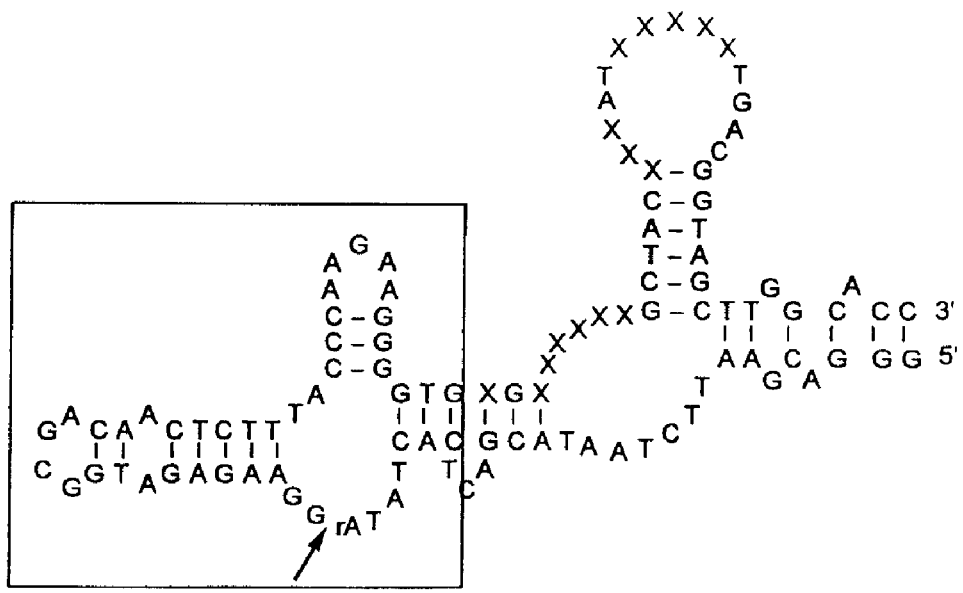
FIG. 7A. (SEQ ID NO: 83) The predicted secondary structure of the G3 deoxyribozyme (Geyer & Sen, 1997). X represents variable sequences. The boxed region was also found in class II Co-DNA predicted by mfold program. The arrows indicate the cleavage site.
Figure 7B:
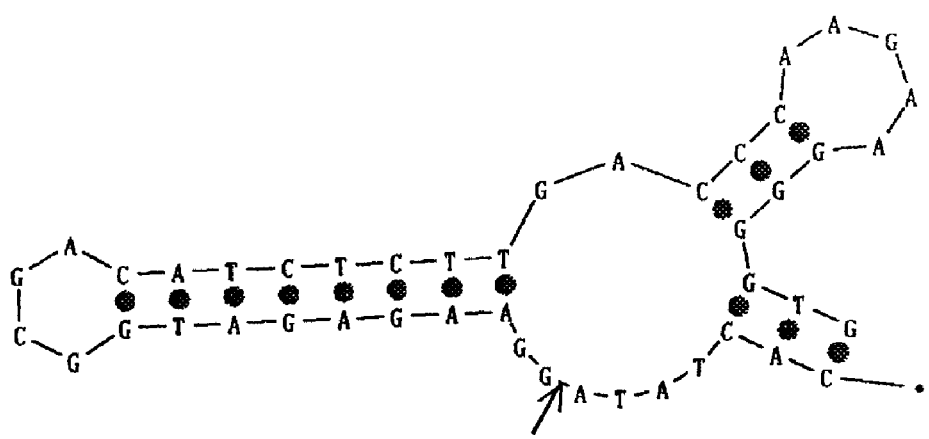
FIG. 7. Comparison of G3 deoxyribozyme with class II Co-DNA.

The class II Co-DNA contains a sequence region (5'-AC-CCAAGAAGGGGTG-3' (SEQ ID NO:10)) that was also found in an RNA-cleaving deoxyribozyme (termed G3) selected by Geyer and Sen (1997) (FIGS. 7A and 7B). The minimal motif predicted for class II Co-DNA shows similarity to that proposed for the G3 deoxyribozyme as well. The G3 deoxyribozyme was believed to be fully active in the absence of any divalent metal ions. Copious use of divalent metal chelating agents, such as EDTA, and accurate trace-metal analysis of the reaction solutions were used to rule out the need of the G3 deoxyribozyme for contaminating levels of divalent metals. As mentioned earlier, the activity of class II Co-DNA was the same in buffer alone or with added $Co^{2+}$ or $Zn^{2+}$, suggesting that this class of Co-DNA most likely contain the divalent metal-independent structure motif.

Effect of Metal Ions on the Activity of the Cis-Cleaving Deoxyribozymes

ZnR17 and Co-18 were examined for their activity dependence on monovalent ions and divalent metal ions other than $Zn^{2+}$ and $Co^{2+}$. In the presence of 1 mM EDTA and without added $Zn^{2+}$ ions, no cleavage was observed with ZnR17 even after two days, strongly suggesting that divalent metal ions are required for the activity of ZnR17. Although the cis-cleaving Zn-DNA was selected in the presence of 500 mM NaCl, NaCl was actually inhibitory to enzymatic activity. With 0-2 M NaCl added to the reaction buffer (100 μM $Zn^{2+}$, 50 mM HEPES, pH 7.0), $k_{obs}$ decreased with increasing NaCl concentration. The deleterious effect of NaCl was also manifested by lowered final percentage of cleavage products. For instance, only 50% of ZnR17 could be cleaved in the presence of 2 M NaCl even after long incubation times, while >95% of the DNA was cleavable in the absence of extra NaCl. Contrary to the Zn-DNA, the activity of Co-18 relies on NaCl and no cleavage was observed in the absence of NaCl. With 1 M NaCl, 8% of Co-18 molecules were cleaved within 5 min, while <0.2% were cleaved in the absence of extra NaCl.

Although the deoxyribozymes were selected using either zinc or cobalt as cofactor, they are also active in other transition metal ions and in $Pb^{2+}$. The cleavage efficiency of ZnR17 followed the trend of $Pb^{2+}>Zn^{2+}>Mn^{2+}\sim Co^{2+}\sim Ca^{2+}>Cd^{2+}>>Ni^{2+}>Mg^{2+}$. It is noteworthy that the cleavage rate in $Ca^{2+}$ was much higher than in $Mg^{2+}$, a similar trend was observed with the Mg5 deoxyribozyme. The order of Co-18 activity is as follow: $Zn^{2+}>Pb^{2+}\sim Co^{2+}>Ni^{2+}>Cd^{2+}\sim Mn^{2+}>Mg^{2+}\sim Ca^{2+}$. In general, both ZnR17 and Co-18 are more active in transition metal ions than in alkaline-earth metals, and higher activities were achieved with $Pb^{2+}$, $Co^{2+}$ and $Zn^{2+}$. The preference of the selected deoxyribozymes for $Co^{2+}$ and $Zn^{2+}$ reflected their selection criteria. A similar trend ($Pb^{2+}>Zn^{2+}>Mn^{2+}>Mg^{2+}$) was also observed with all four RNA-cleaving deoxyribozymes selected in parallel by Breaker and Joyce using one of the four metal ions ($Pb^{2+}$, $Zn^{2+}$, $Mn^{2+}$, $Mg^{2+}$) as cofactor (1995). The proposed secondary structures of the deoxyribozymes selected in $Pb^{2+}$ and $Mg^{2+}$ have been reported (Breaker & Joyce, 1994, 1995). No structure similarity was observed between ZnR17 and those RNA-cleaving deoxyribozymes.

SUMMARY

Using in vitro selection technique, several groups of RNA-cleaving deoxyribozymes were isolated using $Zn^{2+}$ or $Co^{2+}$ as cofactor. No common sequence or structural features were observed between the Co(II)-dependent and the Zn(II)-dependent deoxyribozymes, in spite of the chemical similarities between these two transition metal ions. The deoxyribozymes selected in $Zn^{2+}$ share a common motif with the 8-17 and the Mg5 deoxyribozymes isolated under different conditions, including the use of different cofactors. Both the Co-DNA and the Zn-DNA exhibited higher activity in the presence of transition metal ions than in alkaline earth metal ions, which are the most commonly adopted metal cofactors by naturally occurring ribozymes.

Example 2

Deoxyribozyme as a Biosensor for $Pb^{2+}$ Detection

This Example describes a fluorescence-based biosensor for the detection of $Pb^{2+}$. The biosensor utilizes a deoxyribozyme developed in Example 1 (termed 17E) combined with fluorescence technology to allow quantitative and real time measurements of catalytic activity. Because catalytic activity is dependent on $Pb^{2+}$, the biosensor provides real-time, quantitative, and sensitive measurements of $Pb^{2+}$ concentrations.

Materials and Methods Used in this Example

Oligonucleotides

The oligonucleotides were purchased from Integrated DNA Technology Inc. The cleavable substrate (Rh-17DS) is a DNA/RNA chimera with the sequence 5'-ACTCAC-TATrAGGAAGAGATG-3' (SEQ ID NO:2), in which rA represents a ribonucleotide adenosine. This RNA base is replaced with a DNA base for the non-cleavable substrate (Rh-17DDS) (SEQ ID NO:11) used in the control experiment. Both substrates are covalently linked at the 5' end with 6-carboxytetramethylrhodamin through NHS-ester conjugation. The deoxyribozyme (17E-Dy) is labeled at the 3'-end with Dabcyl via CPG phosphoramidite and has the sequence 5'-CATCTCTTCTCCGAGCCGGTCGAAATAGTGAGT-3' (SEQ ID NO:1). All the oligonucleotides were purified by denaturing 20% polyacrylamide gel electrophoresis to ensure 100% labeling with the fluorescent dyes Fluorescence Spectroscopy The enzyme-substrate complex was prepared with 50 mM each of 17E-Dy and Rh-17DS in 50 mM NaCl, 50 mM HEPES (pH 7.5) with a volume of 600 µl. The sample was heated at 90° C. for 2 min and cooled to 5° C. over 15 min to anneal the enzyme and substrate strands together. Steady-state and slow kinetic fluorescence spectra were collected with a SLM 8000S photon counting fluorometer. Polarization artifacts were avoided by using "magic angle" conditions. The steady-state emission spectra were collected from 570 to 700 nm ($\lambda_{ex}$=560 nm). The time-dependent DNA enzyme catalyzed substrate cleavage was monitored at 580 nm at 2 s intervals. To initiate the reaction, 1-2 µl of concentrated divalent metal ion solution was injected into the cuvette using a 10 µl syringe while the DNA sample in the cuvette was constantly stirred.

DNA-Based Sensor of Metal Ions

An in vitro selected DNA enzyme from Example 1 (termed 17E) that is capable of cleaving a lone RNA linkage within a DNA substrate (termed 17DS) (FIG. 5) was chosen for use as a DNA-based, fluorescent biosensor of metal ions. Assays of this enzyme indicate a highly $Pb^{2+}$ dependent activity with $k_{obs}$=6.5 $min^{-1}$ at pH 6.0 and $K_{apparent}$=13.5 $\mu M^{35}$. The fluorosensor was constructed by labeling the 5'-end of the substrate with the fluorophore 6-carboxytetramethylrhodamin (TAMRA) and the 3'-end of the enzyme strand with 4-(4'-dimethylaminophenylazo)benzoic acid) (Dabcyl). Dabcyl serves as a universal fluorescence quencher. Steady-state fluorescence spectra were obtained by exciting the sample at 560 nm and scanning its emission from 570 to 700 nm.

When the substrate (Rh-17DS) was hybridized to the enzyme strand (17E-Dy), the fluorescence of TAMRA was quenched by the nearby Dabcyl (FIG. 8). Upon addition of $Pb^{2+}$, this quenching was eliminated and the fluorescence of TAMRA increased by ~400%. Little change in the fluorescence signal occurred with addition of $Pb^{2+}$ to the substrate alone or to the complex of the enzyme and a non-cleavable all DNA substrate with identical sequence. These findings show that the change in fluorescent signal with Rh-17DS/17E-Dy results from a DNA enzyme-catalyzed substrate cleavage, followed by product release.

Figure 9A:
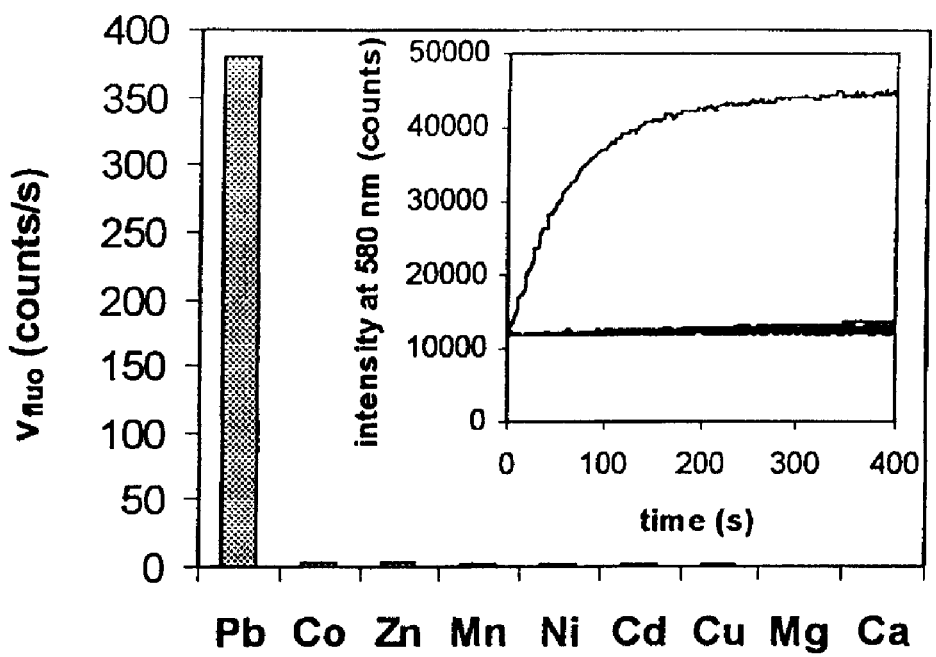
FIG. 9A. with 500 nM M(II) in 50 mM HEPES (pH 7.5); The inserted graph shows the change of fluorescence intensity at 580 nm in response to the addition of M(II). The curve with dramatic change was collected in Pb(II), the other curves were collected in one of the other eight divalent metal ions.
Figure 9B:
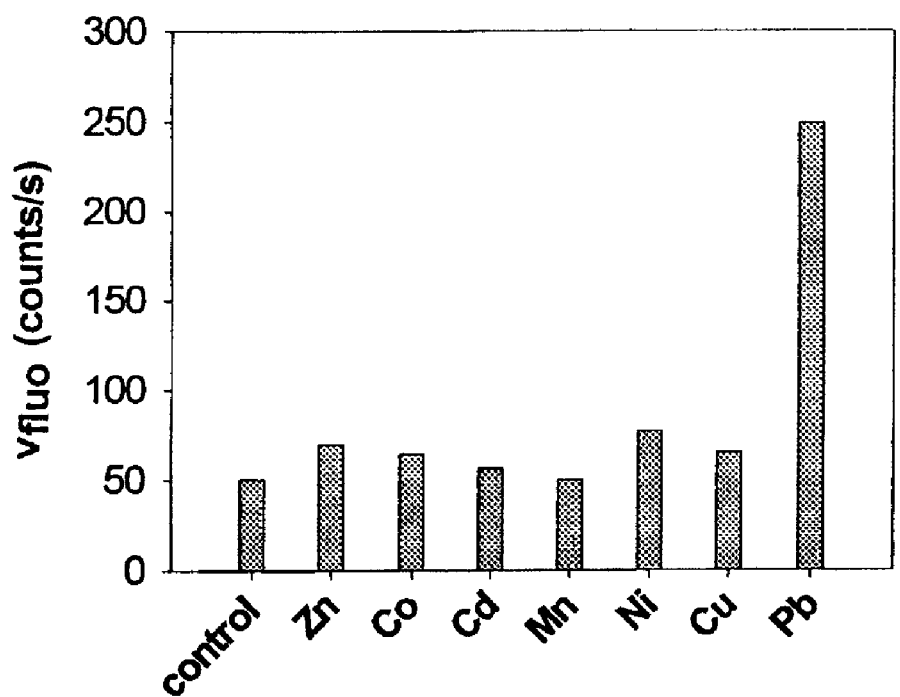
FIG. 9B. with 500 nM M(II) in 100 mM NaCl, 1 mM $Mg^{2+}$, 1 mM $Ca^{2+}$ and 50 mM HEPES (pH 7.5).

The substrate cleavage reaction was monitored in real time with fluorescence spectroscopy. Like the ratiometric, anisotropy, or lifetime-based method, kinetic fluorescence measurement is independent of sampling conditions such as illumination intensity and sample thickness (Oehme & Wolfbeis, 1997). In order to determine the selectivity of the catalytic DNA sensor, the fluorescence change ($\lambda_{em}$=580 nm, $\lambda_{ex}$=560 nm) of Rh-17DS/17E-Dy upon addition of nine different divalent metal ions that are known to be active toward DNA/RNA cleavage (FIG. 9A) was monitored. At the same concentration, $Pb^{2+}$ caused the most rapid change in fluorescence with a rate of 380 counts·$s^{-1}$ at 500 nM $Pb^{2+}$, pH 7.5. The sensitivity toward $Pb^{2+}$ was >80 times higher than other divalent metal ions (FIG. 9A). Remarkably, this trend of selectivity was maintained even under simulated physiological conditions containing 100 mM NaCl, 1 mM $Mg^{2+}$, and 1 mM $Ca^{2+}$ (FIG. 9B). Furthermore, the signal response to $Pb^{2+}$ was not affected by the presence of equal amounts of each of these divalent metal ions. Therefore, this DNA enzyme sensor is well suited for selective monitoring $Pb^{2+}$ in the presence of other metal ions.

Figure 10A:
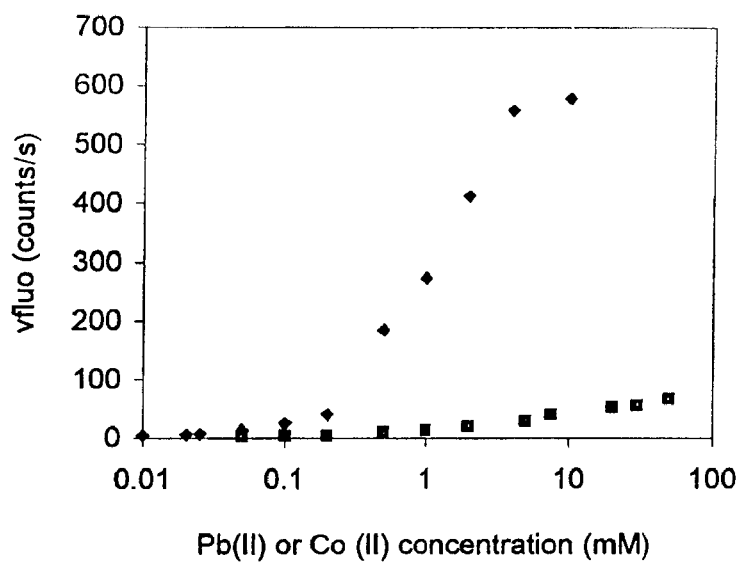
FIG. 10A. The initial rate ($v_{fluo}$) increased with the concentration of $Pb^{2+}$ (♦) and $Co^{2+}$ (■) over a range of three orders of magnitude.
Figure 10B:
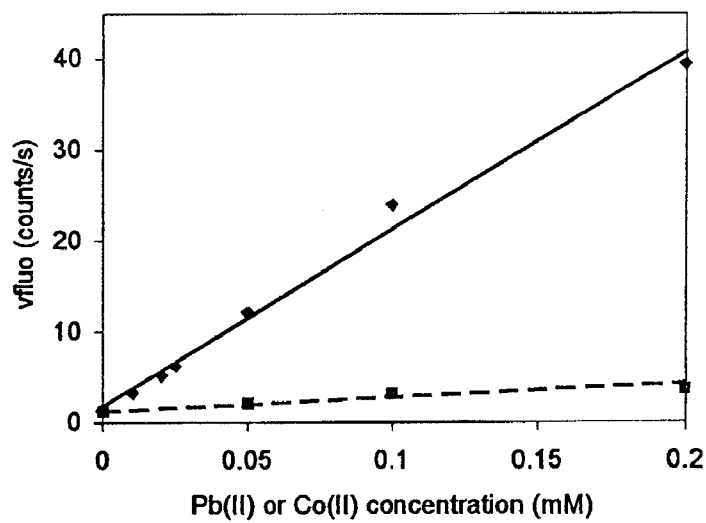
FIG. 10B. At low concentrations, $v_{fluo}$ increased linearly with $Pb^{2+}$ (♦) or $Co^{2+}$ (■) concentration.

In addition to the selectivity of the DNA enzyme probe for $Pb^{2+}$ over other metal ions, the range of $Pb^{2+}$ concentrations which give rise to a fluorescent response is also important. As shown in FIG. 10A, the rate of fluorescence change increased with $Pb^{2+}$ concentration up to 4 µM. The detection limit for $Pb^{2+}$ is around 10 nM, ~50 fold less than the toxic level defined by the Center for Disease Control.

Example 3

DNA Chip Comprising an Array of Nucleic Acid Enzymes

This prophetic example describes the production of and use of a DNA chip for sensing ions, in particular heavy metal ions.

The first step towards the application of deoxyribozymes in heavy metal sensing is to obtain various deoxyribozymes with different metal specificity and affinity. In vitro selection will be carried out to isolate a variety of deoxyribozymes. A detailed description of the selection protocol can be found in Example 1. Each family of deoxyribozyme will be specific for different divalent metal ions (e.g. $Pb^{2+}$, $Hg^{2+}$, $Zn^{2+}$, $Co^{2+}$, $Cd^{2+}$, $Ni^{2+}$, $Mn^{2+}$, etc). Within each family, different sequences will have different affinities of the specified metal ion.

Figure 11A:
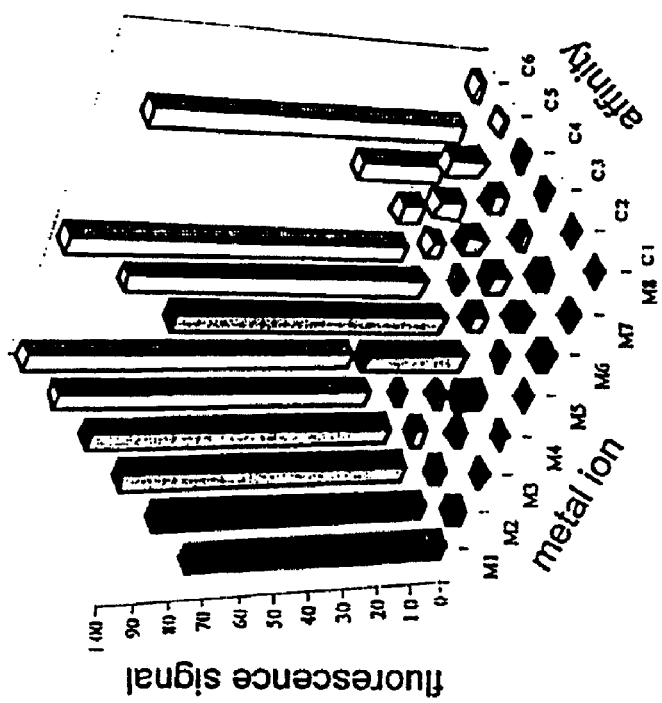
FIG. 11A. The array of deoxyribozymes with different metal specificity and affinity on the DNA chip for metal ion sensing.

These deoxyribozymes and their substrates will then be arrayed onto a DNA chip with one dimension for metal ion specificity and the other for affinity of the corresponding metal (FIG. 11). The enzyme strands immobilized on the chip at 3'-ends can be synthesized on the chip using photolithographic methods (Fodor et al., 1991; Pease et al., 1994) or can be synthesized off-chip and then attached to the chip using various methods (Joos et al., 1997; O'Donnell-Maloney et al., 1997; Guschin et al., 1997). The 5'-end of the enzyme strand will be labeled with a fluorophore. The 3'-end of the substrate strand will be labeled with a fluorescence quencher, which can be a fluorescent or non-fluorescent moiety. For example, guanidine base is an efficient quencher of fluorescein.

Figure 11B:
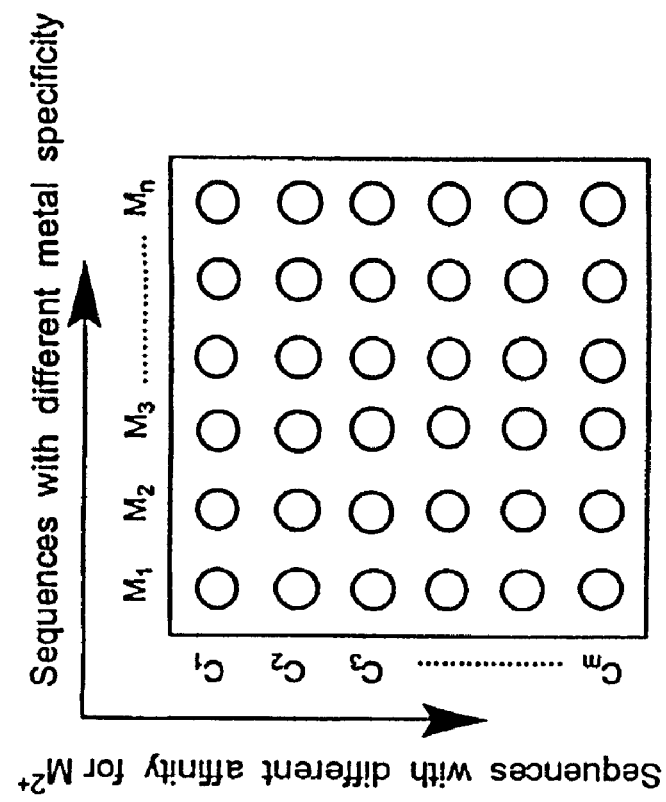
FIG. 11B. Quantitative and qualitative detection of metal ions using the metal ion-sensing deoxyribozyme chip. The z-axis represents the fluorescence intensity change upon the exposure of the chip to the sample under examination. The change in the fluorescence intensity is caused by the deoxyribozyme-catalyzed substrate cleavage in the presence of a specific kind and concentration of metal ion.

Hybridization of the enzyme and substrate will result in the quenching of the donor fluorescence. Upon exposure to the sample containing the active metal ion, the substrate will be cleaved and products will dissociate, resulting in strong fluorescence of the dye attached to the enzyme strand. The metal ion species can be qualitatively identified based on the metal specificity of different families of deoxyribozymes. A hypothetical sample result is shown in FIG. 11B. The pattern of fluorescence intensity shows that there are three kinds of metal (M1, M4, and M6) in the sample.

The concentration of the metal ion under inspection can be quantified with deoxyribozymes with different metal affinity. Given a certain concentration of the metal ion, different sequences within the same family will have different cleavage efficiencies due to their different threshold in response to the metal concentration. The metal concentration applied may exceed the saturation concentration of those having higher affinity; therefore full cleavage will occur within a certain time and present strong fluorescence. On the other hand, the substrates of those with lower affinity will only be partly cleaved and emit weaker fluorescence. The sample hypothetical result shown in FIG. 11B shows high (c1), medium (c4), and low (c6) concentrations of M1, M4, and M6, respectively.

The fluorescence patterns with respect to different deoxyribozyme sequences will be compared with standard calibration maps. After de-convolution of the fluorescence pattern, direct information can be obtained about the identity and concentration of metal ions in the samples.

REFERENCES

Breaker, R. R.; Joyce, G. F. *Chem. Biol.* 1995, 2, 655-660.

Breaker, R. R & Joyce, G. F. A DNA enzyme that cleaves RNA. *Chem. Biol.* 1, 223-229 (1994).

Breaker, R. R. DNA enzymes. *Nat. Biotechnol.* 15, 427-431 (1997).

Cadwell, R. C.; Joyce, G. F. *PCR Methods Appl.* 1992, 2, 28-33.

Cadwell, R. C.; Joyce, G. F. *PCR Methods Appl.* 1994, 3, S136-S140.

Carmi, N., Shultz, L. A. & Breaker, R. R. In vitro selection of self-cleaving DNAs. *Chem. Biol.* 3, 1039-1046 (1996).

Chapman, K. B.; Szostak, J. W. *Curr. Opin. Struct. Biol.* 1994, 4, 618-622.

Ciesiolka, J.; Gorski, J.; Yarus, M. *RNA* 1995, 1, 538-550.

Ciesiolka, J.; Yarus, M. *RNA* 1996, 2, 785-793.

Conaty, J.; Hendry, P.; Lockett, T. *Nucleic Acids Res.* 1999, 27, 2400-2407.

Conn, M. M.; Prudent, J. R.; Schultz, P. G. *J. Am. Chem. Soc.* 1996, 118, 7012-7013.

Cuenoud, B. & Szostak, J. W. A DNA metalloenzyme with DNA ligase activity. *Nature* 375, 611-614 (1995).

Czarnik, A. W. Desperately seeking sensors. *Chem. Biol.* 2, 423-428 (1995).

Dai, X.; De Mesmaeker, A.; Joyce, G. F. *Science* 1995, 267, 237-240.

Deo, S. & Godwin, H. A. A Selective, Ratiometric Fluorescent Sensor for $Pb^{2+}$. *J. Am. Chem. Soc.* 122, 174-175 (2000).

Earnshaw & Gait, "Modified Oligoribonucleotides as site-specific probes of RNA structure and function," *Biopolymers* (John Wiley & Sons, Inc.) 48:39-55, 1998.

Ekland, E. H.; Szostak, J. W.; Bartel, D. P. *Science* 1995, 269, 364-370.

Ekland, E. H.; Bartel, D. P. *Nature* 1996, 382, 373-376.

Famulok, M. *Curr. Opin. Struct. Biol.* 1999, 9, 324-329.

Faulhammer, D.; Famulok, M. *Angew. Chem., Int. Ed Engl.* 1997, 35, 2837-2841.

Fodor, S. P. A., Read, J. L., Pirrung, M. C., Stryer, L., Lu, A. T. & Solas, D. (1991). Light-directed, spatially addressable parallel chemical synthesis. *Science* 251: 767-773.

Frank, D. N.; Pace, N. R. *Proc. Natl. Acad. Sci. U.S.A.* 1997, 94, 14355-14360.

Geyer, C. R.; Sen, D. *Chem. Biol* 1997, 4, 579-593.

Godwin, H. A. & Berg, J. M. A Fluorescent Zinc Probe Based on Metal-Induced Peptide Folding. *J. Am. Chem. Soc.* 118, 6514-6515 (1996).

Guschin, D., Yershov, G., Zaslavsky, A., Gemmell, A., Shick, V., Proudnikov, D., Arenkov, P. & Mirzabekov, A. (1997). Manual manufacturing of oligonucleotide, DNA, and protein microchips. *Anal. Biochem.* 250: 203-211.

Hennrich, G.; Sonnenschein, H.; Resch-Genger, U. *J. Am. Chem. Soc.* 1999, 121, 5073-5074.

Illangasekare, M.; Yarus, M. *J. Mol. Biol.* 1997, 268, 631-639.

Imperiali, B., Pearce, D. A., Sohna Sohna, J.-E., Walkup, G. & Torrado, A. Peptide platforms for metal ion sensing. *Proc. SPIE-Int. Soc. Opt. Eng.* 3858, 135-143 (1999).

Jhaveri, et al., Designed Signaling Aptamers that Transduce Molecular Recognition to Changes in Fluorescence Intensity, *Journal of the American Chemical Society;* 2000; 122(11); 2469-2473.

Joos, B., Kuster, H. & Cone, R. (1997). Covalent attachment of hybridizable oligonucleotides to glass supports. *Anal. Biochem.* 247: 96-101.

Joyce, G. F. *Curr. Opin. Struct. Biol.* 1994, 4, 331-336.

Koizumi, M.; Soukup, G. A.; Kerr, J. N. Q.; Breaker, R. R. *Nat. Struct. Biol.* 1999, 6, 1062-1071.

Lakowicz, J. R. In *Principles of Fluorescence Spectroscopy;* 2nd ed.; Kluwer Academic/Plenum: New York, 1999.

Lee, M., & Walt, D. R. A fiber-optic microarray biosensor using aptamers as receptors. *Anal Biochem* 282(1): 142-146, 2000.

Lehman, N.; Joyce, G. F. *Nature* 1993, 361, 182-185.

Li, J., Zheng, W., Kwon, A.H. & Lu, Y. In vitro selection and characterization of a highly efficient Zn(II)-dependent RNA-cleaving deoxyribozyme. *Nucleic Acids Res.* 28, 481-488 (2000).

Li, Y.; Sen, D. *Nat. Struct. Biol.* 1996, 3, 743-747.

Li, Y.; Breaker, R. R. *Proc. Natl. Acad. Sci. U.S.A.* 1999, 96, 2746-2751.

Li, Y.; Liu, Y.; Breaker, R. R. *Biochemistry* 2000, 39, 3106-3114.

Lohse, P. A.; Szostak, J. W. *Nature* 1996, 381, 442-444.

Lorsch, J. R.; Szostak, J. W. *Nature* 1994, 371, 31-36.

Miyawaki, A., et al. Fluorescent indicators for $Ca^{2+}$ based on green fluorescent proteins and calmodulin. *Nature* 388, 882-887 (1997).

O'Donnell-Maloney, M. J., Tang, K., Koester, H., Smith, C. L. & Cantor, C. R. (1997). High-Density, Covalent Attachment of DNA to Silicon Wafers for Analysis by MALDI-TOF Mass Spectrometry. *Anal. Chem.* 69: 2438-2443.

Oehme, I. & Wolifbeis, O. S. Optical sensors for determination of heavy metal ions. *Mikrochim. Acta* 126, 177-192 (1997).

Pan, T. & Uhlenbeck, O. C. A small metalloribozyme with a two-step mechanism. *Nature* 358, 560-563 (1992).

Pan, T.; Dichtl, B.; Uhlenbeck, O. C. *Biochemistry* 1994, 33, 9561-9565.

Pearce, D. A.; Walkup, G. K.; Imperiali, B. *Bioorg. Med Chem. Lett.* 1998, 8, 1963-1968.

Pease, A. C., Solas, D., Sullivan, E. J., Cronin, M. T., Holmes, C. P. & Fodor, S. P. A. (1994). Light-generated oligonucleotide arrays for rapid DNA sequence analysis. *Proc. Natl. Acad. Sci. U.S.A.* 91: 5022-5026.

Piccirilli, J. A.; McConnell, T. S.; Zaug, A. J.; Noller, H. F.; Cech, T. R. *Science* 1992, 256, 1420-1424.

Pley, H. W.; Flaherty, K. M.; McKay, D. B. *Nature* 1994, 372, 68-74.

Potyrailo, R. A.; Conrad, R. C.; Ellington, A. D.; Hieftje, G. M. *Anal. Chem.* 1998, 70, 3419-3425.

Potyrailo, R. A., Conrad, R. C., Ellington, A. D. & Hieftje, G. M. (1999). Adapting Selected Nucleic Acid Ligands (Aptamers) to Biosensors. *Anal. Chem.* 70: 3419-3425.

Prudent, J. R.; Uno, T.; Schultz, P. G. *Science* 1994, 264, 1924-1927.

Robertson, M. P.; Ellington, A. D. *Nat. Biotechnol.* 1999, 17, 62-66.

Robertson, M. P.; Ellington, A. D. *Nucleic Acids Res.* 2000, 28, 1751-1759.

Roth, A.; Breaker, R. R. *Proc. Natl. Acad. Sci. U.S.A.* 1998, 95, 6027-6031.

Rurack, K., Kollmannsberger, M., Resch-Genger, U. & Daub, J. A Selective and Sensitive Fluoroionophore for HgII, AgI, and CuII with Virtually Decoupled Fluorophore and Receptor Units. *J. Am. Chem. Soc.* 122, 968-969 (2000).

Santoro, S. W.; Joyce, G. F. *Proc. Natl. Acad. Sci. U.S.A.* 1997, 94, 4262-4266.

Santoro, S. W., Joyce, G. F., Sakthivel, K., Gramatikova, S. & Barbas, C. F., III RNA Cleavage by a DNA Enzyme with Extended Chemical Functionality. *J. Am. Chem. Soc.* 122, 2433-2439 (2000).

Scott, W. G.; Finch, J. T.; Klug, A. *Cell* 1995, 81, 991-1002.

Tang and Breaker, *Proc. Natl. Acad. Sci. USA,* 97, 5784-5789 (2000).

Tarasow, T. M.; Tarasow, S. L.; Eaton, B. E. *Nature* 1997, 389, 54-57.

Thompson, R. B., Maliwal, B. P., Feliccia, V. L., Fierke, C. A. & McCall, K. Determination of Picomolar Concentrations of Metal Ions Using Fluorescence Anisotropy: Biosensing with a "Reagentless" Enzyme Transducer. *Anal. Chem.* 70, 4717-4723 (1998).

Tsang, J.; Joyce, G. F. *Methods Enzymol.* 1996, 267, 410-426.

Tsien, R. Y. Fluorescent and photochemical probes of dynamic biochemical signals inside living cells. in *Fluorescent Chemosensors for Ion and Molecule Recognization* (ed. Czarnik, A. W.) 130-46 (American Chemical Society, Washington, D.C., 1993).

Tuerk, C.; Gold, L. *Science* 1990, 249, 505-510.

Uphoff, K. W.; Bell, S. D.; Ellington, A. D. *Curr. Opin. Struct. Biol.* 1996, 6, 281-288.

Vaish, N. K.; Heaton, P. A.; Fedorova, O.; Eckstein, F. *Proc. Natl. Acad. Sci. U.S.A.* 1998, 95, 2158-2162.

Walkup, G. K. & Imperiali, B. Design and Evaluation of a Peptidyl Fluorescent Chemosensor for Divalent Zinc. *J. Am. Chem. Soc.* 118, 3053-3054 (1996).

Wecker, M.; Smith, D.; Gold, L. *RNA* 1996, 2, 982-994.

Wiegand, T. W.; Janssen, R. C.; Eaton, B. E. *Chem. Biol.* 1997, 4, 675-683.

Wilson, C.; Szostak, J. W. *Nature* 1995, 374, 777-782.

Winkler, J. D., Bowen, C. M. & Michelet, V. Photodynamic Fluorescent Metal Ion Sensors with Parts per Billion Sensitivity. *J. Am. Chem. Soc.* 120, 3237-3242 (1998).

Wittmann, C., Riedel, K. & Schmid, R. D. Microbial and Enzyme sensors for environmental monitoring. *Handb. Biosens. Electron. Noses*, 299-332 (1997).

Zhang, B.; Cech, T. R. *Nature* 1997, 390, 96-100.

Zillmann, M.; Limauro, S. E.; Goodchild, J. *RNA* 1997, 3, 734-747.

The invention claimed is:

1. A biosensor comprising:
   (a) a nucleic acid enzyme dependent on an ion to produce a product from a substrate;
   (b) the substrate,
   wherein the substrate comprises a fluorophore and the enzyme comprises a quencher of the fluorophore, or the enzyme comprises a fluorophore and the substrate comprises a quencher of the fluorophore, and
   the ion is selected from the group consisting of $K^+$, $Na^+$, $Li^+$, $Tl^+$, $NH_4^+$, $Ag^+$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Hg^{2+}$, $Pt^{2+}$, $Ra^{2+}$, $Ba^{2+}$, $Sr^{2+}$, $Co^{3+}$, $Cr^{3+}$, $Ln^{3+}$, and $Ce^{4+}$.

2. The biosensor of claim 1, wherein the nucleic acid enzyme comprises a deoxyribozyme.

3. The biosensor of claim 1, wherein the nucleic acid enzyme and the substrate comprise separate nucleic acid strands.

4. The biosensor of claim 1, wherein a 5'-end of the substrate comprises the fluorophore.

5. The biosensor of claim 1, wherein a 3'-end of the enzyme comprises the quencher for the fluorophore.

6. The biosensor of claim 1, wherein the fluorophore is TAMRA.

7. The biosensor of claim 1, wherein the quencher is DABCYL.

8. The biosensor of claim 1, wherein the enzyme is linked to a support.

9. The biosensor of claim 1, wherein the substrate comprises at least one ribonucleotide.

10. The biosensor of claim 1, wherein the enzyme comprises the nucleic acid sequence of SEQ ID NO:1.

11. The biosensor of claim 1, wherein the substrate comprises the nucleic acid sequence of SEQ ID NO:2.

12. The biosensor of claim 1, wherein the ion is selected from the group consisting of monovalent ions, divalent ions, trivalent ions, and polyvalent ions.

13. The biosensor of claim 1, wherein the ion is a cation.

14. A biosensor comprising:
   (a) a nucleic acid enzyme dependent on an ion to produce a product from a substrate;
   (b) the substrate,
   wherein the substrate comprises a fluorophore and the enzyme comprises a quencher of the fluorophore, or the enzyme comprises a fluorophore and the substrate comprises a quencher of the fluorophore, and
   the ion is $Pb^{2+}$.

* * * * *

UNITED STATES PATENT AND TRADEMARK OFFICE
CERTIFICATE OF CORRECTION

| | | |
|---|---|---|
| PATENT NO. | : 7,902,353 B2 | Page 1 of 1 |
| APPLICATION NO. | : 11/674042 | |
| DATED | : March 8, 2011 | |
| INVENTOR(S) | : Lu et al. | |

It is certified that error appears in the above-identified patent and that said Letters Patent is hereby corrected as shown below:

Col. 1, line 13, please delete "may" and insert --has--.

Signed and Sealed this
Twenty-first Day of June, 2011

David J. Kappos
*Director of the United States Patent and Trademark Office*

SEQUENCE LISTING

```
<160> NUMBER OF SEQ ID NOS: 88

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Trans-
      cleaving deoxyribozyme 17E

<400> SEQUENCE: 1
catctcttct ccgagccggt cgaaatagtg agt                                   33

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (10)
<223> OTHER INFORMATION: ribonucleotide base

<400> SEQUENCE: 2
actcactata ggaagagatg                                                  20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 3
gtgccaagct taccg                                                       15

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 4
```

```
ctgcagaatt ctaatacgac tcactatagg aagagatggc gac                    43

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule:
      Primer
<220> FEATURE:
<221> NAME/KEY: modified_base
<222> LOCATION: (28)
<223> OTHER INFORMATION: ribonucleotide base

<400> SEQUENCE: 5
gggacgaatt ctaatacgac tcactata                                     28

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence: Synthetic
      DNA Template
<220> FEATURE:
<221> NAME/KEY: modified_base
<222> LOCATION: (20)..(59)
<223> OTHER INFORMATION: variable nucleotides

<400> SEQUENCE: 6
gtgccaagct taccgtcacn nnnnnnnnnn nnnnnnnnnn nnnnnnnnnn nnnnnnnng    60 agatctcgcc atctcttcct atagtgagtc gtattag                           97

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Variant
      of deoxyribozyme named 17E1

<400> SEQUENCE: 7
catctctttt gtcagcgact cgaaatagtg agt                               33

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Synthetic Zn-DNA
<220> FEATURE:
<221> NAME/KEY: modified_base
<222> LOCATION: (2)..(4)
<223> OTHER INFORMATION: variable bases complementary to positions
      8-10
<220> FEATURE:
<221> NAME/KEY: modified_base
<222> LOCATION: (8)..(10)
<223> OTHER INFORMATION: variable bases complementary to positions
      2-4

<400> SEQUENCE: 8
tnnnagcnnn tcgaaatagt                                              20

<210> SEQ ID NO 9
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      Zn-DNA sequence
<220> FEATURE:
<221> NAME/KEY: modified_base
<222> LOCATION: (2)..(4)
<223> OTHER INFORMATION: variable bases complementary to positions
      8-10
<220> FEATURE:
<221> NAME/KEY: modified_base
<222> LOCATION: (8)..(10)
<223> OTHER INFORMATION: variable bases complementary to positions
      2-4

<400> SEQUENCE: 9
tnnnagcnnn acgaa                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Class II
      Co-DNA sequence

<400> SEQUENCE: 10
acccaagaag gggtg                                                    15

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Rh-17DDS

<400> SEQUENCE: 11
actcactata ggaagagatg                                               20

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (39)..(78)
<223> OTHER INFORMATION: variable nucleotides

<400> SEQUENCE: 12
ctaatacgac tcactatagg aagagatggc gacatctcnn nnnnnnnnn nnnnnnnnn     60 nnnnnnnnnn nnnnnnnngt gacggtaagc ttggcac                            97

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 13
```
ctgcagaatt ctaatacgac tcactatagg aagagatggc gac                43

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 14
atctcttttg tcagcgactc gaaatagtgt gttgaagcag ctctagtgac            50

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 15
agccatagtt ctaccagcgg ttcgaaatag tgaagtgttc gtgactatc             49

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 16
ggccatagtt ctaccagcgg ttcgaaatag tgaaatgttc gtgactatc             49

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 17
gccagattag ttctaccagc ggttcgaaat agtgaaatgt tcgtgactat c          51

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 18
atctccaaag atgccagcat gctattctcc gagccggtcg aaatagtgac            50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 19

```
atctccaaag atgcctgcat gctattctcc gagccggtcg aaatagtgac       50
```

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 20

```
atctcgtctc cgagccggtc gaaatagtca ggtgtttcta ttcgggtgac       50
```

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 21

```
atcaccttct ccgagccggt cgaaatagta gttttagta tatctgtgac        50
```

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 22

```
atctcaggtg ttggctgctc tcgcggtggc gagaggtagg gtgatgtgac       50
```

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 23

```
ggtaagcttg gcac                                              14
```

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 24

```
ctgcagaatt ctaatacgac gcactatagg aagagatggc gac              43
```

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 25

```
atctcttgta ttagctacac tgttagtgga tcgggtctaa tctcggtgac       50
```

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 26
gtctcttgta ttagctacac tgttagtgga tcgggtctaa tctcggtgac         50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 27
atctcctgta ttagctacac tgttagtgga tcgggtctaa tctcggtgac         50

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 28
atctcttgta ttagctacac tgttagtggg aacgttatca ttcggtgac          49

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 29
atctcttgac ccaagaaggg gtgtcaatct aatccgtcaa ccatg              45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 30
atctcttgac ccaagaaggg gtgtcaatca aatccgtcaa ccatg              45

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 31
atctcttgac ccaagaaggg gtgtcaatct aatccgtaca accatgacgg taag    54

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 32
atctcttgac ccaagaaggg gtgtcaatct aatccgtcaa ggatgcggta ag            52

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 33
atctcaggtg ttggctgctc ccgcggtggc gggaggtagg gtgatgtgac               50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 34
atctcaggtg ttggcatctc ccgcggtggc gagaggtagg gtgatgtgac               50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 35
atctcaggtg ttggctgctc tcgcggtggc gagaggtagg gtcatgtgac               50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 36
atctcgcagt cgaagcttca ctgttagtgc ggacgggtag acttcgtgac               50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 37
atttcttctg aatcctcaat gttagtggac ctagtcgtag tcgatgtgac               50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 38
atctcggagc cagttagcat aatcttctga atcctcaatg ttagtgtgac        50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 39
atctcggtgt tggctggata gagccggtag gccctatcgt agggtgtgac        50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 40
gtctcttttg tccgcgactc gaaatagtgt gttgaagcag ctctagtgac        50

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 41
agccatagtt ctaccagcgg ttcgaaatag tgaagtgttc gtgactatcg gtaa        54

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 42
ggtaagcttg gcac        14

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 43
ttttgtcagc gactcgaaat agtgtgttga agcagctcta        40

<210> SEQ ID NO 44

```
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 44
ttttgtcagc gactcgaaat agtgtgttga agccgctcta                            40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 45
ttttgtcagc gactcgaaat agtgtattgc agtagatcta                            40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 46
ttttgtcagc gactcgaaat agtgtgttac agttgcccta                            40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 47
ttttgtcagc gactcgaaat agagagtcga cacacctctc                            40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 48
ttttgtcagc gactcgaaat agttagttga accagctctc                            40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 49
ttttgtcagc gactcgaaat agtgagtaag aggagctatc                            40

<210> SEQ ID NO 50
<211> LENGTH: 40
```

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 50
ttttgtcagc gactcgaaat agtgagggga aacagctctc     40

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 51
ttttgtcagc gactcgaaat agttagttga acacctctc      39

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 52
ttttgtcagc gactcgaaat attgagttga agcagatctc     40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 53
ttttgtcagc gacacgaaat agtgagttga ggcggcgctg     40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 54
tttttgcagc gacacgaaat agttagttga agaagctctt    40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 55
ttttgtcagc gactcgaaat agtcagttgt agcagctctt    40

<210> SEQ ID NO 56
<211> LENGTH: 40
<212> TYPE: DNA

<213> ORGANISM: Artificial Sequence
<220> FEATURE:
<223> OTHER INFORMATION: Description of Artificial Sequence: Synthetic
      Zn-DNA

<400> SEQUENCE: 56
ttttgtcagc gactcgaaat agtgcgtaga accagctctc                              40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 57
ttttgtcagc gacacgaaat agtgcggtgt atctgccctc                              40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 58
ttttgtcagc gacacgaaat agtgtgatgt agtagctctc                              40

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 59
ttttgtcagc gacacgaaat agtgtgacga atcatctc                                38

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 60
ttttgtcagc gacacgaaat agtgtgttta agcgctctc                               39

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 61
ttttgtcagc gacacgaaat agtgtgttga agcacgtctc                              40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 62
ttttgtcagc gactcgaaat agtttgttga agcagctctc                          40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 63
ttttgtcagc gactcgaaat agtgtattac agcagctctc                          40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 64
ttttgtcagc gactcgaaat agtgtgttga aacagctatc                          40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 65
ttgtgcatgc tactcgtaat tgtgtctcga agcagctctc                          40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 66
gtcagtcagg tactcgaaaa atagtgttca agccgctgtc                          40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 67
tttttgcagc gactcgaaag attgtgttga ggcggctatc                          40

<210> SEQ ID NO 68
<211> LENGTH: 40
<212> TYPE: DNA
<213> ORGANISM: Artificial Sequence
<220> FEATURE:

```
<223> OTHER INFORMATION: Description of Artificial Sequence: Synthetic
      Zn-DNA

<400> SEQUENCE: 68
ttctctcagc gactaaaaat agtgtgttga agccctctc                                40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 69
tattgtcagt gacccaaaat agtatgttga agcagctctg                               40

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Synthetic
      Zn-DNA

<400> SEQUENCE: 70
ttttgtcagc tactgaaata gtgttttgaa gaagtcctg                                39

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (8)
<223> OTHER INFORMATION: ribonucleotide base

<400> SEQUENCE: 71
tcactatagg aagag                                                         15

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 72
ctcttcagcg atccggaacg gcacccatgt tagtga                                  36

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
```

```
         Synthetic chimeric substrate
<220> FEATURE:
<221> NAME/KEY: modified_base
<222> LOCATION: (8)
<223> OTHER INFORMATION: ribonucleotide base

<400> SEQUENCE: 73
tcactataag aagagatgg                                                  19

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 74
acacatctct gaagtagcgc cgccgtatag tgacgct                              37

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 75
ggagagagau gggugcg                                                    17

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 76
cgcacccagg ctagctacaa cgactctctc c                                    31

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 77
aaguaacuag agaugga                                                    17

<210> SEQ ID NO 78
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 78
cgcaccctcc gagccggacg aagttactt                                           29

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (9)
<223> OTHER INFORMATION: ribonucleotide base

<400> SEQUENCE: 79
ctcactatag gaagagatg                                                       19

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 80
catctcttaa cggggctgtg cggctaggaa gtaatagtga g                              41

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (10)
<223> OTHER INFORMATION: ribonucleotide base

<400> SEQUENCE: 81
actcactata ggaagagatg                                                      20

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
```

-continued

```
<400> SEQUENCE: 82
catctcttct ccgagccggt cgaaatagtg agt                                    33

<210> SEQ ID NO 83
<211> LENGTH: 107
<212> TYPE: DNA
<213> ORGANISM: Artificial Sequence
<220> FEATURE:
<223> OTHER INFORMATION: Description of Combined DNA/RNA Molecule:
      Synthetic chimeric oligonucleotide
<220> FEATURE:
<223> OTHER INFORMATION: Description of Artificial Sequence: Predicted
      secondary structure of the G3 deoxyribozyme
<220> FEATURE:
<221> NAME/KEY: modified_base
<222> LOCATION: (28)
<223> OTHER INFORMATION: ribonucleotide base
<220> FEATURE:
<221> NAME/KEY: modified_base
<222> LOCATION: (67)
<223> OTHER INFORMATION: variable nucleotide
<220> FEATURE:
<221> NAME/KEY: modified_base
<222> LOCATION: (69)..(74)
<223> OTHER INFORMATION: variable nucleotide
<220> FEATURE:
<221> NAME/KEY: modified_base
<222> LOCATION: (80)..(82)
<223> OTHER INFORMATION: variable nucleotide
<220> FEATURE:
<221> NAME/KEY: modified_base
<222> LOCATION: (85)..(89)
<223> OTHER INFORMATION: variable nucleotide

<400> SEQUENCE: 83
gggacgaatt ctaatacgac tcactatagg aagagatggc gacaactctt tacccaagaa      60
ggggtgngnn nnnngctacn nnatnnnnnt gacggtagct tggcacc                   107

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      Co-DNA

<400> SEQUENCE: 84
cactatagga agagatggcg acatctcttg acccaagaag gggtg                      45

<210> SEQ ID NO 85
<211> LENGTH: 44
<212> TYPE: DNA
<213> ORGANISM: Artificial Sequence
<220> FEATURE:
<223> OTHER INFORMATION: Description of Combined DNA/RNA Molecule:
      Synthetic chimeric substrate
<220> FEATURE:
<223> OTHER INFORMATION: Description of Artificial Sequence: Synthetic
      chimeric oligonucleotide
<220> FEATURE:
<221> NAME/KEY: modified_base
<222> LOCATION: (22)
<223> OTHER INFORMATION: ribonucleotide base

<400> SEQUENCE: 85
tgtcaactcg tgactcacta taggaagaga tgtgtcaact cgtg                       44

<210> SEQ ID NO 86
<211> LENGTH: 12
<212> TYPE: DNA
```

```
<213> ORGANISM: Artificial Sequence
<220> FEATURE:
<223> OTHER INFORMATION: Description of Artificial Sequence: Primer
<220> FEATURE:
<223> OTHER INFORMATION: see specification as filed for
      detailed description of preferred embodiments

<400> SEQUENCE: 86
cacgagttga ca                                                              12

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide 17E-C

<400> SEQUENCE: 87
catctcttcc ccgagccggt cgaaatagtg agt                                       33

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: see specification as filed for
      detailed description of preferred embodiments

<400> SEQUENCE: 88
cacgagttga ca                                                              12
```